United States Patent
Hamamoto et al.

(10) Patent No.: US 10,709,617 B2
(45) Date of Patent: Jul. 14, 2020

(54) ABSORBENT ARTICLE WITH FUSION BONDED SIDE SEAMS

(71) Applicant: KAO CORPORATION, Tokyo (JP)

(72) Inventors: Shinji Hamamoto, Shimotsuke (JP); Koji Imai, Utsunomiya (JP); Takuo Yanashima, Utsunomiya (JP)

(73) Assignee: KAO CORPORATION, Tokyo (JP)

( * ) Notice: Subject to any disclaimer, the term of this patent is extended or adjusted under 35 U.S.C. 154(b) by 1228 days.

(21) Appl. No.: 14/895,862

(22) PCT Filed: Jun. 26, 2014

(86) PCT No.: PCT/JP2014/066923
§ 371 (c)(1),
(2) Date: Dec. 3, 2015

(87) PCT Pub. No.: WO2014/208638
PCT Pub. Date: Dec. 31, 2014

(65) Prior Publication Data
US 2016/0120709 A1      May 5, 2016

(30) Foreign Application Priority Data
Jun. 28, 2013   (JP) ................................. 2013-137385

(51) Int. Cl.
*A61F 13/15*     (2006.01)
*A61F 13/20*     (2006.01)
(Continued)

(52) U.S. Cl.
CPC .. *A61F 13/49058* (2013.01); *A61F 13/15739* (2013.01); *A61F 13/15804* (2013.01);
(Continued)

(58) Field of Classification Search
CPC . B29C 66/71; B29C 65/1648; B29C 66/1122; B29C 66/137; B29C 66/3472;
(Continued)

(56) References Cited

U.S. PATENT DOCUMENTS

| 4,115,683 | A |   | 9/1978 | Clark et al. |
| 5,626,574 | A | * | 5/1997 | Sasaki ................... A61F 13/496 |
|           |   |   |        | 156/190 |

(Continued)

FOREIGN PATENT DOCUMENTS

| CN | 1243691 A | 2/2000 |
| CN | 1212106 C | 7/2005 |

(Continued)

OTHER PUBLICATIONS

International Search Report (form PCT/ISA/210), dated Jan. 20, 2015, for International Application No. PCT/JP2014/078296.

(Continued)

*Primary Examiner* — Michele M Kidwell
(74) *Attorney, Agent, or Firm* — Birch, Stewart, Kolasch & Birch, LLP

(57) ABSTRACT

A pull-on diaper 50B of the invention includes an outer cover assembly 3 defining the exterior surface of the diaper. A front body portion F and a rear body portion R of the outer cover assembly 3 are connected to each other along their laterally opposite side edges to form a pair of side seams 4, a waist opening 8, and a pair of leg openings 9. Each side seam 4 has a sealed edge portion 41 where the front body portion side edge 3F and the rear body portion side edge 3R of the outer cover assembly 3 are bonded to each other at a continuous linear fusion bond extending in the longitudinal direction of the side seam and, in part, a non-sealed portion 42 where the front body portion side edge 3F and the rear
(Continued)

body portion side edge 3R of the outer cover assembly face to each other in a non-bonded relationship.

17 Claims, 11 Drawing Sheets

(51) Int. Cl.
*A61F 13/49* (2006.01)
*B29C 65/16* (2006.01)
*A61F 13/496* (2006.01)
*B29C 65/00* (2006.01)
*B29C 65/74* (2006.01)
*A61F 13/84* (2006.01)
*B29L 31/48* (2006.01)

(52) U.S. Cl.
CPC .... *A61F 13/49011* (2013.01); *A61F 13/4963* (2013.01); *A61F 13/84* (2013.01); *B29C 65/1648* (2013.01); *B29C 65/1661* (2013.01); *B29C 65/1696* (2013.01); *B29C 65/7473* (2013.01); *B29C 66/1122* (2013.01); *B29C 66/3472* (2013.01); *B29C 66/431* (2013.01); *B29C 66/723* (2013.01); *B29C 66/72941* (2013.01); *B29C 66/73921* (2013.01); *B29C 66/83433* (2013.01); *B29C 66/83435* (2013.01); *A61F 2013/15878* (2013.01); *A61F 2013/8497* (2013.01); *B29C 65/1619* (2013.01); *B29C 66/137* (2013.01); *B29C 66/71* (2013.01); *B29L 2031/4878* (2013.01)

(58) Field of Classification Search
CPC .............. B29C 66/431; B29C 66/723; B29C 66/83433; B29C 66/83435; A61F 13/15739; A61F 13/49011; A61F 13/49058; A61F 13/4963; A61F 13/84; A61F 2013/15878; A61F 2013/8497; B29L 2031/4878
See application file for complete search history.

(56) References Cited

U.S. PATENT DOCUMENTS

| | | | |
|---|---|---|---|
| 6,234,229 B1 | 5/2001 | Tabuchi | |
| 6,387,083 B1 | 5/2002 | Suzuki | |
| 6,394,991 B1 | 5/2002 | Takei et al. | |
| 6,652,501 B2 * | 11/2003 | Malchow | A61F 13/15756 156/290 |
| 9,808,379 B2 * | 11/2017 | Hamamoto | A61F 13/4963 |
| 2002/0173764 A1 | 11/2002 | Takino et al. | |
| 2003/0100879 A1 * | 5/2003 | Kline | A61F 13/15 604/386 |
| 2003/0213552 A1 | 11/2003 | Chen et al. | |
| 2005/0224472 A1 | 10/2005 | Rasmussen et al. | |
| 2006/0283846 A1 | 12/2006 | Lupinetti et al. | |
| 2007/0032766 A1 | 2/2007 | Liu et al. | |
| 2007/0084553 A1 | 4/2007 | Nakajima et al. | |
| 2008/0145682 A1 | 6/2008 | Rasmussen et al. | |
| 2008/0176023 A1 | 7/2008 | Bager et al. | |
| 2011/0125122 A1 | 5/2011 | Thorson et al. | |
| 2012/0021186 A1 | 1/2012 | Schneider | |
| 2012/0035564 A1 | 2/2012 | Otsubo et al. | |
| 2012/0078212 A1 | 3/2012 | Kobayashi et al. | |
| 2012/0088646 A1 | 4/2012 | Berggren et al. | |
| 2012/0095429 A1 | 4/2012 | Kobayashi et al. | |
| 2012/0283683 A1 * | 11/2012 | Tai | A61F 13/49011 604/385.3 |
| 2012/0289920 A1 | 11/2012 | Otsubo et al. | |
| 2013/0123736 A1 | 5/2013 | Ichikawa et al. | |
| 2013/0139960 A1 | 6/2013 | Maruyama et al. | |
| 2013/0174965 A1 | 7/2013 | Yamamoto et al. | |
| 2015/0064387 A1 * | 3/2015 | Imai | B29C 66/7392 428/57 |
| 2015/0144251 A1 * | 5/2015 | Schoultz | A61F 13/15747 156/73.1 |

FOREIGN PATENT DOCUMENTS

| | | |
|---|---|---|
| CN | 1956836 A | 5/2007 |
| CN | 101068519 A | 11/2007 |
| CN | 101237840 A | 8/2008 |
| CN | 101352921 A | 1/2009 |
| CN | 101746057 A | 6/2010 |
| CN | 102307551 A | 1/2012 |
| CN | 102427791 A | 4/2012 |
| CN | 102458338 A | 5/2012 |
| CN | 102781391 A | 11/2012 |
| CN | 103079514 A | 5/2013 |
| JP | 63-64732 A | 3/1988 |
| JP | 63-118237 A | 5/1988 |
| JP | 64-48690 A | 2/1989 |
| JP | 7-75653 A | 3/1995 |
| JP | 8-38546 A | 2/1996 |
| JP | 9-192863 A | 7/1997 |
| JP | 2000-14697 A | 1/2000 |
| JP | 2001-120595 A | 5/2001 |
| JP | 2001-145659 A | 5/2001 |
| JP | 2004-1507 A | 1/2004 |
| JP | 2004-267335 A | 9/2004 |
| JP | 2005-237768 A | 9/2005 |
| JP | 2008-546540 A | 12/2008 |
| JP | 2009-202502 A | 12/2008 |
| JP | 2009-297300 A | 12/2009 |
| JP | 2010-11584 A | 5/2010 |
| JP | 2010-125654 A | 6/2010 |
| JP | 2010-188629 A | 9/2010 |
| JP | 2011-25006 A | 2/2011 |
| JP | 2011-126011 A | 6/2011 |
| JP | 2011-131556 A | 7/2011 |
| JP | 2012-76343 A | 4/2012 |
| JP | 2012-111076 A | 6/2012 |
| JP | 2013-71282 A | 4/2013 |
| JP | 2013-529149 A | 7/2013 |
| JP | 2013-202182 A | 10/2013 |
| JP | 2013-256109 A | 12/2013 |
| JP | 2013-256133 A | 12/2013 |
| JP | 2014-124398 A | 7/2014 |
| JP | 2014-168904 A | 9/2014 |
| JP | 2015-8944 A | 1/2015 |
| JP | 2015-85091 A | 5/2015 |
| TW | 201201776 A1 | 1/2012 |
| WO | WO 2012/070462 A1 | 5/2012 |
| WO | WO 2013/1723403 A1 | 11/2013 |
| WO | WO 2014/103818 A1 | 7/2014 |

OTHER PUBLICATIONS

Extended European Search Report, dated Jan. 25, 2017, for European Application No, 14817839.5.
International Search Report, issued in PCT/JP2014/066923, dated Sep. 22, 2014.
International Preliminary Report on Patentability and English translation of the Written Opinion of the International Searching Authority (forms PCT/IB/373, PCT/ISA/237 and PCT/IB/338), dated Jan. 7, 2016, for International Application No. PCT/JP2014/066923.
International Preliminary Report on Patentability and English translation of the Written Opinion of the International Searching Authority (Forms PCT/IB/338, PCT/IB/373 and PCT/ISA/237), dated Nov. 27, 2014, for International Application No. PCT/JP2013/063418.
International Search Report dated Jun. 11, 2013, for International Application No. PCT/JP2013/063418.
Extended European Search Report dated Nov. 2, 2015 for Application No. 13790158.3.

\* cited by examiner

A →

ABSORBENT ARTICLE WITH FUSION BONDED SIDE SEAMS

TECHNICAL FIELD

The present invention relates to a pull-on garment having side seams.

BACKGROUND ART

Among known pull-on garments is included a disposable pull-on diaper including an absorbent assembly and an outer cover assembly defining the exterior surface of the garment and having its front body portion and rear body portion connected to each other along their lateral side edges to form a pair of side seams.

In removing a disposable pull-on diaper from a wearer, the diaper is usually torn open into a front body portion and a rear body portion in the side seam. In order to quickly remove a diaper from a body of the wearer at the time of changing the diaper after use, the side seams are preferably configured to be easily torn open. With regard to tearability of side seams, Patent Literature 1 proposes providing side seams with a combination of three levels of bonding strength so as to improve the tearability as well as to maintain a bonding strength enough to prevent tear during use of the diaper.

In the conventional manufacture of absorbent articles such as disposable diapers and sanitary napkins, a heat roller unit has been used widely to join superimposed sheets, and side seams are usually formed by the heat roller unit as will be described later. Laser welding is another known method for joining superimposed sheets. For example, Patent Literature 2 discloses a method for uniting a continuous stack of sheets by fusion bonding, the method comprising transporting a continuous stack of sheets on a rotating drum while deforming the sheets in conformity to the peripheral surface of the drum, the drum having a laser beam transmissive window, and directing a laser beam from the inside of the rotating drum to the moving stack of sheets.

A disposable pull-on diaper is generally manufactured through the steps of making a continuous length of diaper (also referred to as a continuous diaper web) having a plurality of diapers connected to each other in one direction (machine direction), connecting the superimposed front and rear body portions of the outer cover assembly at positions corresponding to side seams by a bonding means, such as a heat roller unit, and severing the thus bonded portions by a cutting means, such as a cutter, to obtain individual diapers. The side seams of the thus manufactured conventional disposable pull-on diapers are butt-type seams formed by superimposing both lateral side edge portions of the front and rear body portions in a face-to-face relationship. Because the side edge of the butt-type side seam protrudes outwardly from the neighboring part of the diaper, the side seam is readily recognizable by the naked eye.

Patent Literature 3 below discloses a disposable pull-on diaper which is produced by bonding both side edges of the front and rear body portions of a non-stretch backsheet while leaving a leg elasticized portion unbonded to form a slit in each side seam.

CITATION LIST

Patent Literature

Patent Literature 1: U.S. Pat. No. 6,394,991B1
Patent Literature 2: JP 2010-188629A
Patent Literature 3: JP 8-38546A

SUMMARY OF INVENTION

Because the butt-type side seams manufactured through the above described steps have a large bond width, and the outer cover assembly is strongly pressed when bonded to itself, feels relatively hard and rough and therefore leave room for improvement in wearer comfort and feel of the outer cover assembly to the touch. On the other hand, if the bond width of the outer cover assembly is made smaller, the side seams will be less recognizable by the naked eye while the diaper is worn or in a relaxed, contracted state and may be difficult to recognize visually. If the side seams are not readily recognized by the naked eye especially while the diaper is worn, when a caregiver, e.g., the mother of an infant wearer, takes off the diaper from the wearer after use, there is a likelihood that the caregiver has trouble finding the side seams and removing the diaper.

The present invention provides a pull-on garment including an outer cover assembly defining the exterior surface of the garment, the outer cover assembly having a front body portion and a rear body portion, the front body portion and the rear body portion of the outer cover assembly being connected to each other along their laterally opposite side edges to form a pair of side seams, a waist opening, and a pair of leg openings. The side seams each have: a sealed edge portion where the edge of the front body portion and the edge of the rear body portion of the outer cover assembly are bonded to each other at a continuous linear fusion bond extending in the longitudinal direction of the side seam; and, in part, a non-sealed portion where the edge of the front body portion and the edge of the rear body portion of the outer cover assembly face to each other in a non-bonded relationship.

The invention also provides a first method for making the pull-on garment of the invention.

The first method includes: a superimposing and pressing step in which the front body portion and the rear body portion of an outer cover assembly web are superimposed on each other, and a region of the superimposed front body portion and the rear body portion where a side seam is to be formed is placed in a pressed state; and a side seam forming step in which the region where a side seam is to be formed is irradiated in the pressed state with a laser beam through a light transmissive window extending in a direction intersecting the machine direction of the outer cover assembly web thereby to sever the web and, at the same time, fusion-bond the edges of the superimposed front body portion and rear body portion resulting from the severing to form the side seam. The side seam forming step includes irradiating the region where a side seam is to be formed with a laser beam through the light transmissive window having a wide portion and a narrow portion different in width, so that the sealed edge potion is formed by the laser beam which passes through the narrow portion, and the non-sealed portion is formed by the laser beam which passes through the wide portion.

The invention also provides a second method for making the pull-on garment of the invention.

The second method includes: a superimposing and pressing step in which the front body portion and the rear body portion of an outer cover assembly web are superimposed on each other, and a region of the superimposed front body portion and the rear body portion where a side seam is to be formed is placed in a pressed state; and a side seam forming step in which the region where a side seam is to be formed is irradiated in the pressed state with a laser beam through a light transmissive window extending in a direction intersecting the machine direction of the outer cover assembly web thereby to sever the web and, at the same time, fusion-bond the edges of the superimposed front body portion and rear body portion, the edges resulting from the severing to form the side seam. The side seam forming step is carried out using a support member having a high level portion and a low level portion different in height toward the side of the outer cover assembly web, the high level portion and the low level portion being located at the vicinity of the light transmissive window and on an outer surface of the support member on which the outer cover assembly web is to be contacted. The side seam forming step includes applying the laser beam to; a region of the outer cover assembly web that is highly pressed by the high level portion to form the sealed edge portion; and to a region of the outer cover assembly web that is relatively weakly pressed by the low level portion to form the non-sealed portion.

BRIEF DESCRIPTION OF DRAWINGS

FIG. 6(a) and FIG. 6(b) schematically illustrate a continuous diaper web in its flattened state while being introduced into the laser bonding device shown in FIG. 1, of which FIG. 6(a) is a top view of a hold down member with a part cut away, and FIG. 6(b) is a cross-sectional view of FIG. 6(a) taken along line II-II.

DESCRIPTION OF EMBODIMENTS

The invention relates to a side-seamed disposable pull-on garment of which the side seams are excellent in softness and feel to the touch and readily recognizable by the naked eye and methods for making the same.

The disposable pull-on garment of the invention includes an outer cover assembly defining the exterior surface of the garment. The outer cover assembly has a front body portion and a rear body portion, and the front body portion and the rear body portion are connected to each other along their laterally opposite side edges to form a pair of side seams, a waist opening, and a pair of leg openings. One of the main characteristics of the invention consists in introducing a device (means) for improving visual recognizability of side seams (hereinafter also referred to as side seam visibility improving means) to the above configured garment in the cases when each side seam has a sealed edge portion where the edge of the front body portion and the edge of the rear body portion of the outer cover assembly are bonded to each other by a fusion bond extending continuously in the longitudinal direction of the side seam.

Introducing the side seam visibility improving means in the manufacture of pull-on garments is particularly effective for garments whose pair of side seams are formed by the step of severing a continuous web of superimposed front and rear halves of the outer cover assembly into individual garment articles by, for example, directing a laser beam to predetermined positions of the continuous web and, at the same time, fusion bonding each severed edge of the superimposed front and rear body portions of the outer cover assembly. Because side seams formed by the above described step have low visual recognizability while the garment is worn (during use), it is beneficial to improve their visual recognizability during use, especially so as to facilitate tearing the side seams and removing the garment from the wearer's body. Because such side seams have low visual recognizability also when the garment is in a relaxed, contracted state, it is beneficial to improve the visual recognizability of the side seams of the garment in its relaxed, contracted state before use so as to help discrimination between front and back sides and between left and right sides of the garment.

In what follows, the fundamental technique relating to pull-on garments and a method for making them to which the side seam visibility improving means of the invention is applicable will be described first. The pull-on garment of the invention having the side seam visibility improving means and methods for making the same will next be described with reference to their preferred embodiments.

[I] Fundamental Technique

Figure 1:
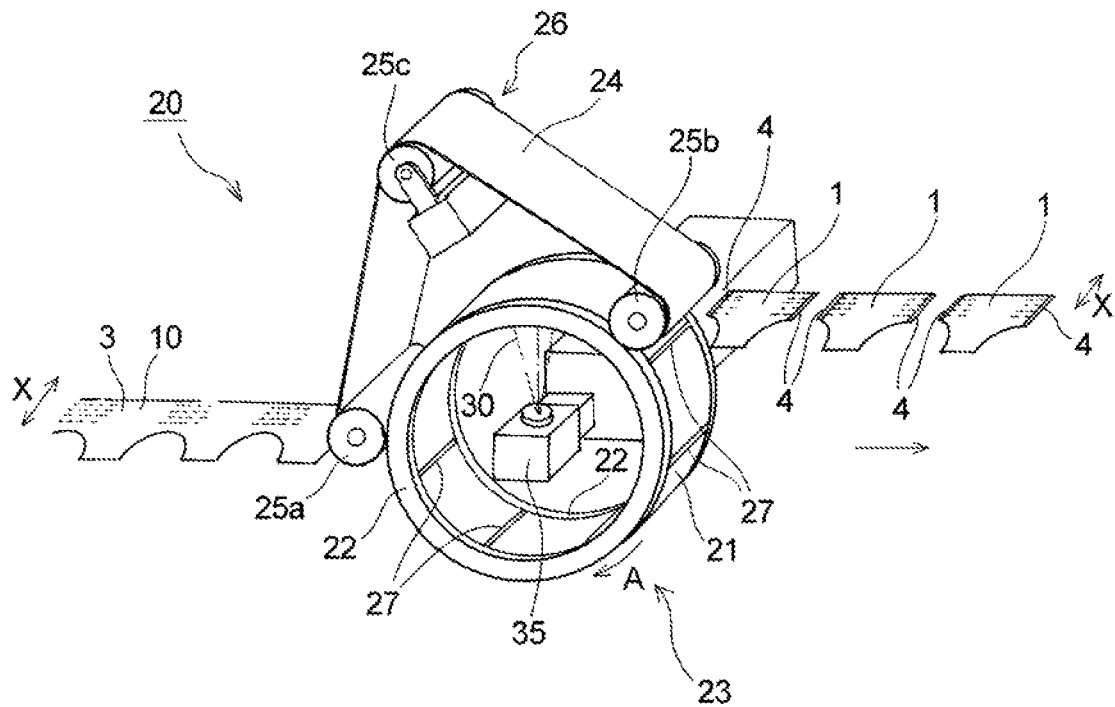
FIG. 1 is a schematic perspective view of an embodiment of the method of the invention for making a disposable pull-on diaper using a laser bonding device that is applicable to the production of the disposable pull-on diaper of the invention.
Figure 2:
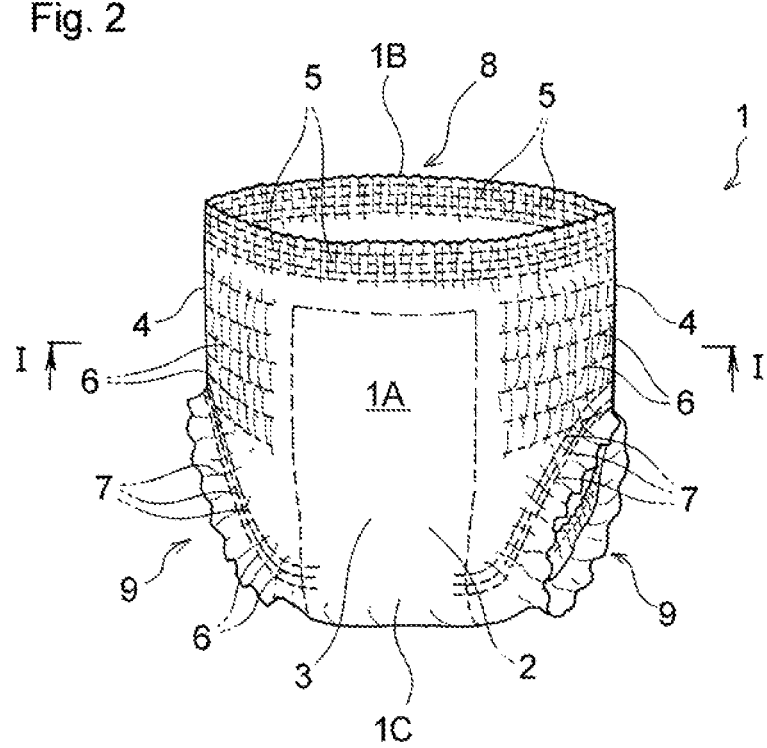
FIG. 2 is a schematic perspective view of a disposable pull-on diaper made by implementing the method shown in FIG. 1 according to a fundamental technique.
Figure 3:
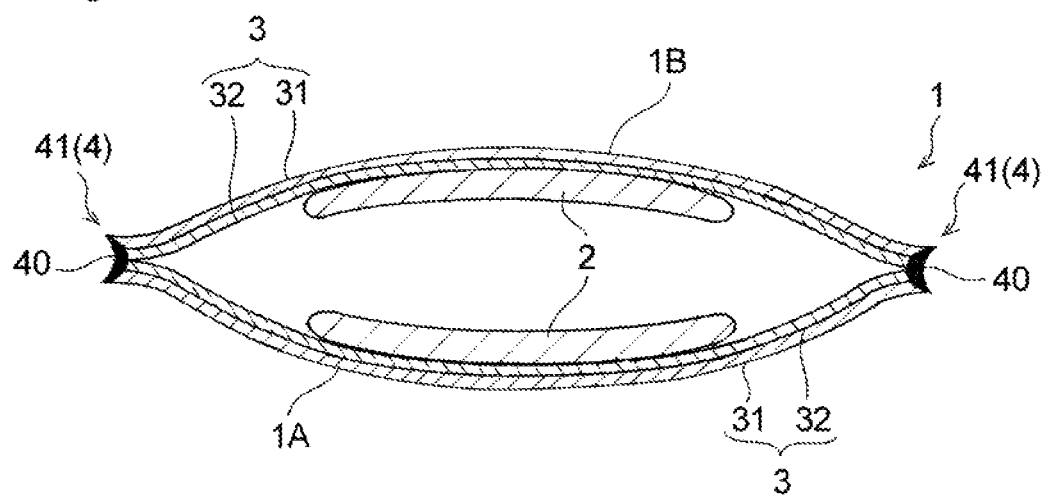
FIG. 3 is a schematic cross-sectional view of the diaper of FIG. 2 taken along line I-I.
Figure 4:
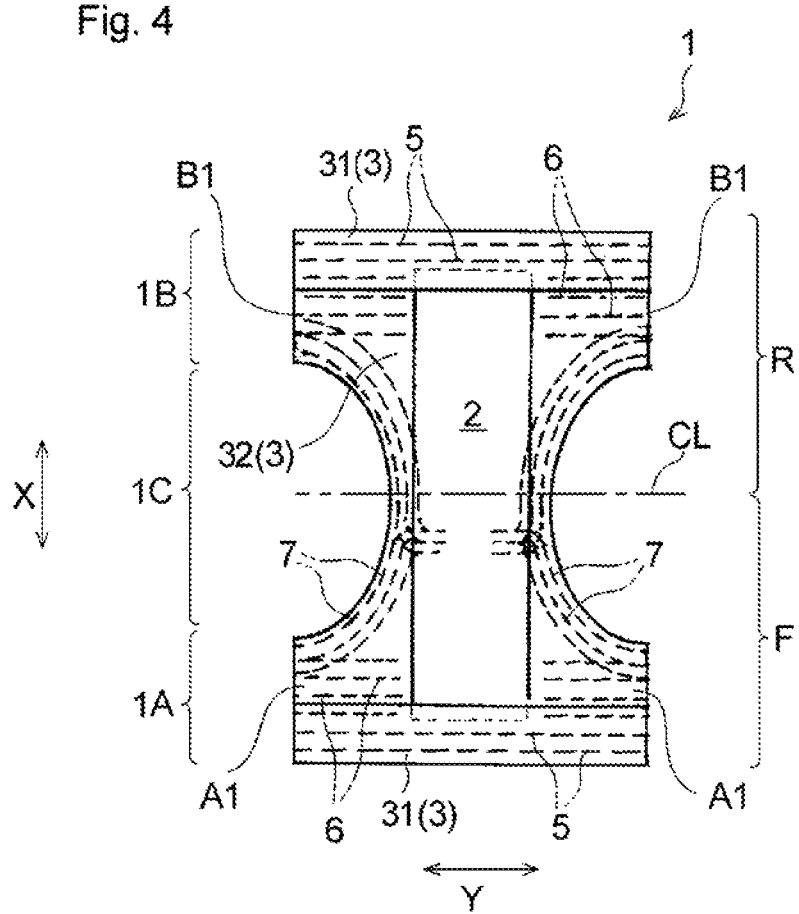
FIG. 4 is a plan view of the diaper shown in FIG. 2 in its flat-out, uncontracted state.

FIG. 1 schematically illustrates a method for making a disposable pull-on diaper using a laser bonding device that is applicable to the production of a disposable pull-on diaper as an embodiment of the method of the invention. The diaper 1 that is the product of the method using the laser bonding device is, as illustrated in FIGS. 2 through 4, a disposable pull-on diaper including an absorbent assembly 2 and an outer cover assembly 3 defining the exterior surface of the garment. Both lateral side edges A1 of the front body portion F (front portion 1A) of the outer cover assembly 3 extending longitudinally of the outer cover assembly 3 (in direction X) and both lateral side edges B1 of the rear body portion R (rear portion 1B) of the outer cover assembly 3 extending longitudinally of the outer cover assembly 3 (in direction X) are connected to each other to form a pair of side seams 4, a waist opening 8, and a pair of leg openings 9. The outer cover assembly 3 is disposed on the non-skin facing surface side of the absorbent assembly 2 and having the absorbent assembly 2 fixed thereto. Each side seam 4 is formed of a sealed edge portion 41 of the outer cover assembly where the front body portion side edge and the rear body portion side edge are bonded to each other at a continuous linear fusion bond 40 extending in the longitudinal direction of the side seam 4.

The diaper 1 has a longitudinal direction (or direction X) corresponding to the front-to-rear direction of a wearer and a lateral (or transverse) direction (or direction Y) perpendicular to the direction X in a plan view in its flat-out, uncontracted state as illustrated in FIG. 4. The diaper 1 is divided into a crotch portion 1C that is to be worn about the crotch of a wearer while worn, a front portion 1A that is located forward of the crotch portion 1C, and a rear portion 1B that is located backward of the crotch portion 1C. The outer cover assembly has a concave edge on either lateral side thereof in the crotch portion 1C for providing a pair of leg openings 9. As illustrated in FIG. 4, the diaper 1 is sectioned by a transverse centerline CL into a front body portion F and a rear body portion R.

As used herein, the term "skin facing surface" refers to the surface of a pull-on garment or a member constituting the garment, such as the absorbent assembly, facing the wearer's skin while worn. The term "non-skin facing surface" refers to the surface of a pull-on garment or a member constituting the garment facing away from the wearer's skin while worn. The direction X of the diaper 1 is coincident with the direction extending in parallel to the longer side of the diaper or its constituent member, the absorbent assembly 2 (longitudinal direction of the diaper or the absorbent assembly 2), and the direction Y is coincident with the lateral or transverse direction of the disposable diaper or its constituent member, the absorbent assembly 2.

As illustrated in FIG. 4, the absorbent assembly 2 has an oblong shape that is relatively longer in one direction (direction X) and includes a topsheet (not shown) defining the skin-facing surface, a backsheet (not shown) defining the non-skin facing surface, and a liquid-retentive absorbent member (not shown) interposed between the topsheet and the backsheet. The absorbent member is oblong in the direction X. The absorbent assembly 2 is bonded to a central region of the outer cover assembly 2 by any known bonding method, such as adhesive bonding, with its longitudinal direction coincident with the direction X of the diaper 1 in a flat-out, uncontracted state. As used herein, the term "flat-out, uncontracted state" means a state in which a pull-on absorbent diaper is opened by tearing the side seams apart and with every elastic member straightened up to its design dimension (the dimension of the diaper in a flat-out configuration with any influences of elastic members eliminated).

As illustrated in FIGS. 2 through 4, the outer cover assembly 3 is composed of an outer sheet 31 defining the exterior surface of the diaper 1 (the non-skin facing surface of the outer cover assembly 3), an inner sheet 32 disposed on the inner side of the outer sheet 31 to provide the inner side of the diaper 1 (the skin facing surface of the outer cover assembly 3), and a plurality of thread-like or ribbon-like elastic members 5, 6, and 7 fixed between the two sheets 31 and 32 with adhesive. The two sheets 31 and 32 are bonded to each other at predetermined positions by a bonding means, such as an adhesive or heat sealing.

The outer cover assembly 3 (the outer sheet 31 and the inner sheet 32) contains a resinous material and is formed mainly of the resinous material. The outer sheet 31 and the inner sheet 32 of the outer cover assembly 3 are each exemplified by nonwoven fabric, film, or a nonwoven fabric/film laminate each containing, as a resinous material, a thermobondable synthetic resin, such as polyethylene, polyethylene terephthalate, or polypropylene. Examples of the nonwoven fabric include an air-through nonwoven fabric, a heat-rolled nonwoven fabric, a hydroentangled nonwoven fabric, a spun-bonded nonwoven fabric, or a melt-blown nonwoven fabric.

The method for making the diaper 1 includes: a superimposing and pressing step in which the front and rear body portions of a continuous outer cover assembly web are superimposed on each other, and a region of superimposed front and rear body portions where a side seam is to be formed is placed in a pressed state; and a side seam forming step in which a laser beam is applied to the pressed region of the continuous outer cover assembly web where a side seam is to be formed through a light transmissive window 27 elongated in a direction intersecting the machine direction (direction A) of the web thereby to sever the web and, at the same time, fusion bond the edges of the superimposed body portions resulting from the severing to form the side seam 4. The superimposing and pressing step is preceded by an absorbent assembly fixing step in which the absorbent assembly 2 is fixed to the continuous outer cover assembly web 3 (the outer sheet 31 and the inner sheet 32).

Figure 5:
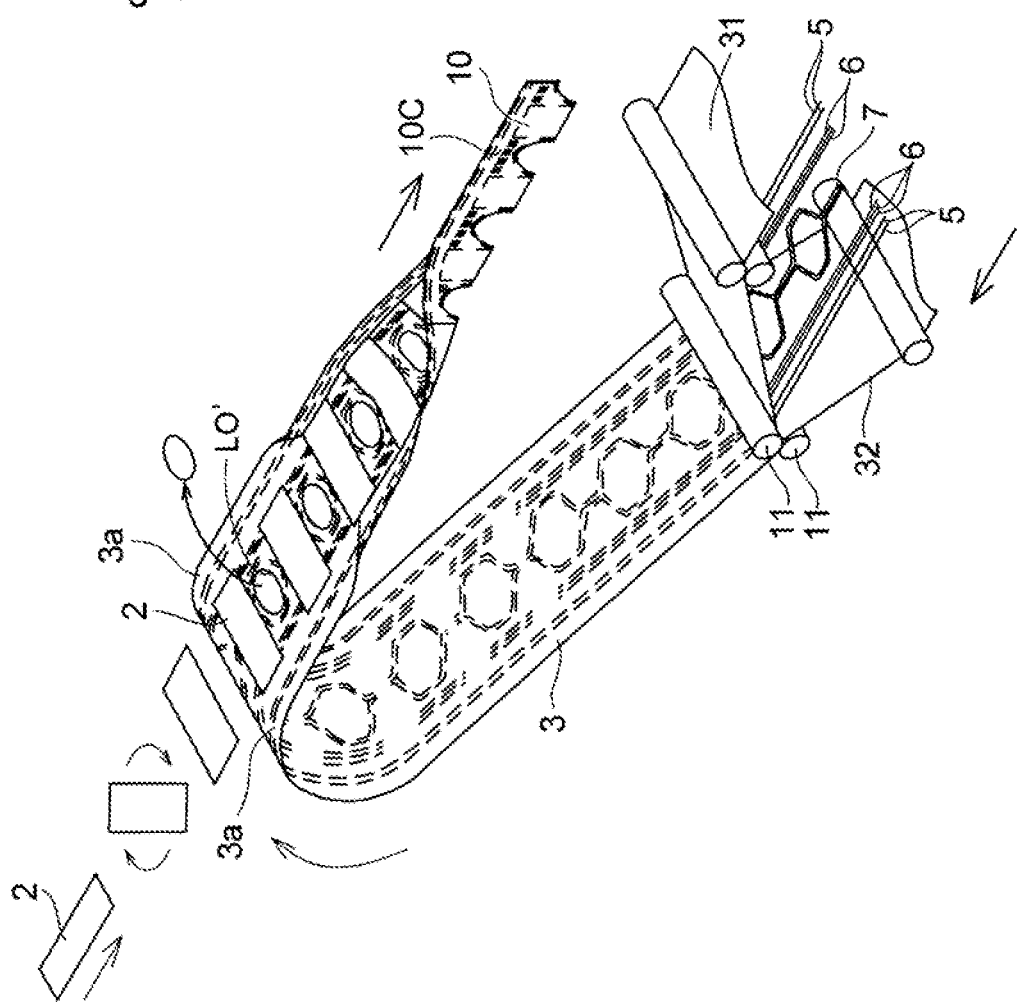
FIG. 5 is a schematic perspective illustrating the steps for making a continuous length of diaper (continuous diaper web) shown in FIG. 1.

Specifically, in the superimposing and pressing step of the manufacturing method of the diaper 1, as illustrated in FIG. 5, the continuous outer cover assembly web 3 (the outer sheet 31 and the inner sheet 32) having the absorbent assemblies 2 fixed thereto is lengthwise folded to superimpose the front and rear body portions of the web 3, thereby to make a continuous diaper web 10 having a plurality of seamless, disposable pull-on diapers (disposable pull-on diaper precursors) connected to each other in one direction. In the side seam forming step, as illustrated in FIG. 1, the continuous outer cover assembly web 3 of the continuous diaper web 10 is irradiated with a laser beam 30 to be severed into individual articles. Simultaneously with the severing, the severed edges of the plurality of layers of the outer cover assembly 3 (the superimposed outer sheet 31 and the inner sheet 32) are fused and bonded together to continuously produce disposable pull-on diapers 1 each having the side-seamed outer cover assembly 3.

More specifically, as illustrated in FIG. 5, a continuous length of outer sheet 31 and a continuous length of inner sheet 32 are continuously fed from the respective stock rolls (not shown), and waist elastic members 5 forming waist gathers, below-waist elastic members 6 forming below-waist gathers, and leg elastic members 7 forming leg gathers are arranged between the two continuous lengths of inner and outer sheet in their stretched state at predetermined stretch ratios. The leg elastic members 7 are arranged in a prescribed pattern forming a thigh circumference by means of a known rocking guide (not shown) that moves reciprocally in a direction perpendicular to the machine direction. A hot-melt adhesive is previously applied to prescribed locations of one or both of the continuous length of outer sheet 31 and the continuous length of inner sheet 32 on the side facing to the other sheet using an unshown adhesive applicator before the continuous sheets are superimposed on each other. When the elastic members, such as the waist elastic members 5 and the below-waist elastic members 6, provided in their stretched state straddle the regions to be severed by a laser beam (the locations where side seams 4 are to be funned, which are indicated with reference 10C in FIGS. 6(a) and 6(b) and will also each referred to as a target region 10C), it is preferred to previously apply an adhesive to these regions and their vicinities in order to prevent the elastic members from excessively retracting or being drawn out after the severing. A hot-melt adhesive may previously be applied at intervals to the waist elastic members 5 and the below-waist elastic members 6 using an adhesive applicator (not shown) before they are arranged between the two sheets 31 and 32.

As illustrated in FIG. 5, the continuous outer sheet 31 and the continuous inner sheet 32 having the waist elastic members 5, the below-waist elastic members 6, and the leg elastic members 7 fixed therebetween in their stretched state are introduced into the nip between a pair of nip rollers 11 and pressed to make a continuous outer cover assembly web 3 composed of the continuous sheets 31 and 32 and the elastic members 5, 6, and 7 fixed between the continuous sheets 31 and 32 in their stretched state. In the step of making the continuous outer cover assembly web 3, a plurality of bonds (not shown) at which the continuous outer sheet 31 and the continuous inner sheet 32 are bonded to each other may preferably be formed between adjacent below-waist elastic members 6 using a bonding means (not shown), such as a pair of sealing roller and an anvil roller.

Thereafter, if necessary, the part of the below-waist elastic members 6 and the part of the leg elastic members 7 that are to overlap the absorbent assembly 2 disposed later are deelasticized by press cutting into segments using an elastic member precutting means (not shown). The elastic member precutting means is exemplified by the elastic member cutting unit described in JP 2002-253605A, which is used in the production of a composite stretch sheet.

As illustrated in FIG. 5, an adhesive, such as a hot-melt adhesive, is applied to the absorbent assemblies 2 that have been made in a separate process line, and the absorbent assemblies 2 are successively turned 90 degrees and fixed at intervals onto the continuous inner sheet 32 of the continuous outer cover assembly web 3. The adhesive for fixing the absorbent assembly may previously be applied not to the absorbent assembly 2 but a predetermined location of the continuous inner sheet 32 where the absorbent assembly 2 is to be placed.

The continuous outer cover assembly web 3 having the absorbent member 2 is processed to make a leg hole LO' inside the ring formed of the leg elastic members 7 as illustrated in FIG. 5. The leg hole making is achieved in a conventional manner commonly used in the manufacture of this type of articles using, for example, a rotary cutter or a laser cutter. While in the embodiment illustrated in FIG. 5 the leg holes are made after the absorbent assembly 2 is placed on the continuous outer cover assembly web 3, the leg hole making may precede the placement of the absorbent assembly 2.

The continuous outer cover assembly web 3 is then folded lengthwise (in the direction parallel to the machine direction of the outer cover assembly 3). Specifically, as illustrated in FIG. 5, an edge portion 3a on either side of the continuous outer cover assembly web 3 extending in the machine direction is folded inward to cover and fix the longitudinal end of the absorbent assembly 2, and then the continuous outer cover assembly web 3 is folded lengthwise in two to obtain a continuous diaper web 10 (superimposing substep of the superimposing and pressing step).

The thus prepared continuous diaper web 10 is processed by directing a laser beam using a laser bonding device 20 to form a pair of side seams 4 as shown in FIG. 1 (side seam forming step) thereby continuously making disposable pull-on diapers 1 having the side-seamed outer cover assembly 3.

The laser bonding device 20 will then be described. As illustrated in FIG. 1, the laser bonding device 20 includes: a hollow cylindrical drum 23 rotatably driven in direction of arrow A; a cylindrical (annular) support member 21 defining the outer periphery of the cylindrical drum 23; a laser processing head 35 inside the hollow cylindrical drum 23 from which head a laser beam 30 is emitted toward the support member 21; and a belt-type pressing unit 26 having an endless pressing belt (a hold down member) 24.

The laser bonding device 20 has a tension adjusting mechanism (not shown) that adjusts the tension of the pressing belt 24 trained about the periphery of the annular support member 21 (the periphery of the cylindrical drum 23). The pressure applied to the continuous diaper web 10 (continuous superimposed sheets) by the support member 21 and the pressing belt 24 is adjusted appropriately by adjusting the tension.

The support member 21 defines the peripheral surface (the surface with which the web to be processed is brought into contact) of the cylindrical drum 23. The support member 21 is fixed in between a pair of annular frames 22 that define both transverse edges of the cylindrical drum 23. The support member 21 is made of a heat-resistant material, such as a metallic material (e.g., iron, aluminum, stainless steel, or copper) or ceramics.

Figure 6A:
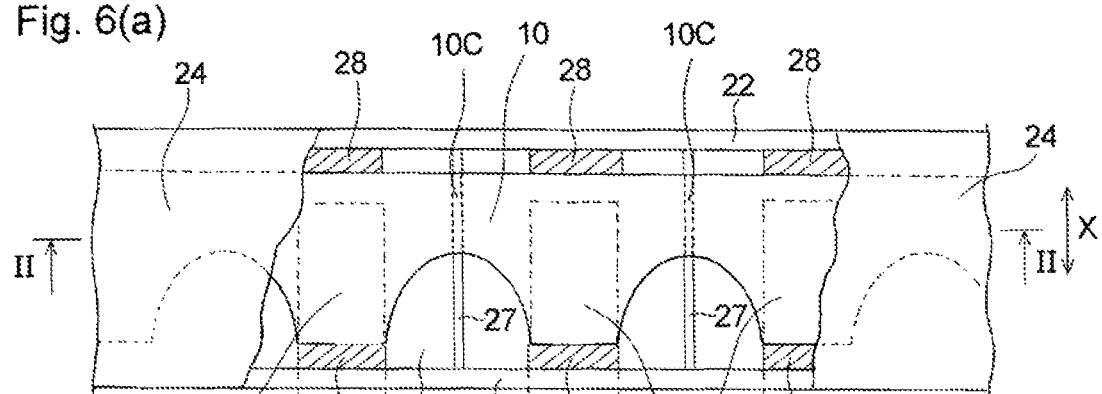
Figure 6B:
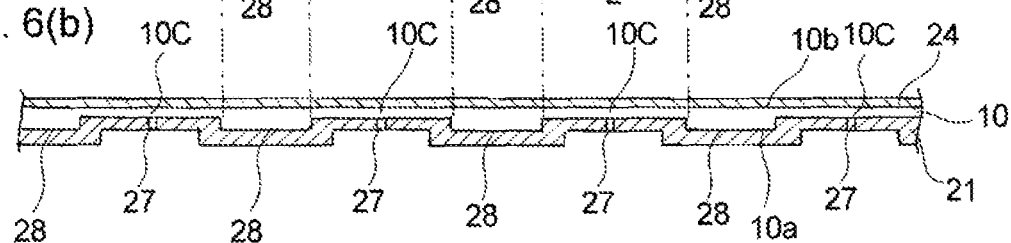

The support member 21 has a light transmissive window 27 through which a laser beam can pass. As illustrated in FIGS. 1, 6(a), and 6(b), the support member 21 has slit-like openings 27 going through the thickness of the support member 21 as light transmissive windows. The opening 27 is rectangular in a plan view with its longitudinal direction coincident with a direction intersecting the machine direction A of the continuous diaper web 10 (continuous outer cover assembly web 3), specifically the direction parallel to the rotational axis of the cylindrical drum 23, which is indicated with letter X in FIG. 6(a). A plurality of the openings 27 are spaced from one another in the circumferential direction of the cylindrical support member 21. The support member 21 allows a laser beam to pass through each opening 27 but does not through other than the openings 27. The support member 21 having the openings 27 can be made by, for example, (1) making openings 27 at predetermined locations of the support member 21 formed of a single annular member having the same circumferential length as the annular frame 22 by etching, punching, laser machining or a like technique or (2) arranging a plurality of arcuate rectangular segments between the pair of frames 22 at a predetermined spacing in the circumferential direction of the frames 22 instead of using a single annular member. In the case of the method (2), the space between adjacent segments corresponds to the slit-like opening 27. The method (2) is adopted in the fundamental technique described herein and first and second embodiments of the production method according to the invention described hereinafter.

The support member 21 used in the hereinafter described first embodiment of the production method of the invention (support member 21A) has openings 27A (light transmissive window) each formed of a wide portion and narrow portions different in width. The support member 21 used in the hereinafter described second embodiment of the production method of the invention (support member 21B) has, on the side with which the continuous outer cover assembly 3 is to contact, a high level and a low level portion projecting toward the outer cover assembly 3 to different heights in a vicinity of the opening 27 (light transmissive window).

The support member 21, the pressing belt (hold down member) 24, and the continuous diaper web 10 (continuous outer cover assembly web) in between are depicted in FIGS. 6(a) and 6(b) as horizontally moving from left to right for the sake of easy illustration only. In fact, they move in a curve around the periphery of the cylindrical drum 23.

In the laser bonding device 20 (a device for making sealed sheets the edges of which are fusion bonded together to form a sealed edge portion), the light transmissive window for allowing a laser beam to pass through is the slit-like opening 27 going through the thickness of the support member 21. Accordingly, the target region 10C (the region to be severed) of the continuous diaper web 10 (continuous superimposed sheets) that aligns the opening 27 is not held between the support member 21 and the pressing belt (hold down member) 24, with only the pressing belt 24 applied thereto. Strictly speaking, therefore, the pressure created between the two members 21 and 24 is not applied to the target region 10C. While the target region 10C per se is not held between the two members 21 and 24, the vicinities of the target region 10C, i.e., the regions of the continuous diaper web 10 near the opposite edges of the opening 27 are held between the two members 21 and 24. Therefore, the target region 10C is immobilized when irradiated with a laser beam, so that the severed edges resulting from the severing of the continuous diaper web 10 by the laser irradiation are also immobile. In other words, the target region 10C of the continuous diaper web 10 (the region of the superimposed sheets aligning the opening 27) is restrained by the pressing force exerted between the two members 21 and 24, i.e., virtually under the influence of the pressing force.

As illustrated in FIG. 6(b), the support member 21 has a plurality of recesses 28 on its peripheral surface (the surface with which the material to be processed is brought into contact) at a predetermined interval in the circumferential direction. The slit-like opening 27 is formed in the region (i.e., a raised portion) located between adjacent recesses 28. The opening 27 is located at the middle of the raised portion in the circumferential direction.

In the case that the recesses 28 are formed in the outer surface of the support member 21 in the way described above, when the thickness of the continuous diaper web 10 (continuous superimposed sheets) is not uniform due to relatively thick portions (e.g., the portions where the absorbent assembly 2 is placed), the continuous diaper web 10 can be introduced onto the peripheral surface of the support member 21 with registration such that the relatively thick portion may fit into the recess 28. By so introducing the continuous diaper web 10 onto the support member 21, the surface of the continuous diaper web 10 with which the pressing belt (hold down member) 24 comes into contact (hereinafter referred to as a second side 10b) is almost flat as illustrated in FIG. 6(b). As a result, upon being pressed under the pressing belt 24, the part of the continuous diaper web 10 located on the raised portion having the opening 27 is uniformly pressed in its thickness direction under a given pressure by the pressing belt 24 and by the wrap of the continuous diaper web 10 around the support member 21 with a predetermined wrap-tension. When the part thus kept in a pressed state is irradiated with a laser beam to be severed, the resultant severed edges of the plurality of sheets constructing the part are fusion bonded to one another more securely thereby to further assure the improvement in fusion bonding strength of the side seams (sealed edge portions) 4.

The belt-type pressing unit 26 has an endless pressing belt (hold down member) 24 and three rollers 25a, 25b, and 25c rotatable with the pressing belt 24 trained thereabout. The rollers 25a, 25b, and 25c may each be a drive roller or a driven roller driven by the pressing belt 24. The pressing belt 24 runs at the same speed as the cylindrical drum 23 (the support member 21) either by using at least one drive roller chosen from the rollers 25a, 25b, and 25c or being driven by the cylindrical drum 23. The temperature of the support member 21 and the pressing belt 24 are preferably maintained in a predetermined range by, for example, air cooling or water cooling.

The pressing belt (hold down member) 24 may be a heat-resistant metal or resin belt capable of withstanding the heat generated during processing. For example, a metal belt made of iron, aluminum, or stainless steel may be used. While the pressing belt 24 is usually made of a material impermeable to laser light that is applied to the material to be processed (i.e., the continuous outer cover assembly web 3), a pressing belt 24 made of a laser light-permeable material may also be usable.

As illustrated in FIG. 1, the laser processing head 35 is provided in the hollow space of the hollow cylindrical drum 23 from which head a laser beam 30 is emitted toward the support member 21 defining the outer periphery of the cylindrical drum 23. The laser processing head 31 is a galvanometer scanner (a device having a mirror on a motor axis) that scans with a laser beam 30. The laser processing head 31 includes: a mechanism for reciprocating a laser beam 30 in a direction parallel to the axial direction of the cylindrical drum 23 (the direction indicated by reference letter X in FIG. 6(a)); a mechanism for moving the irradiation point (the location at which the continuous diaper web 10 on the support member 21 is irradiated with the laser beam 30) along the circumferential direction of the cylindrical drum 23; and a mechanism for maintaining a constant beam diameter of the laser beam 30 on the peripheral surface of the cylindrical drum 23. So constructed, the laser processing mechanism is capable of moving the irradiation point of the laser beam 30 as desired in both the circumferential direction of the cylindrical drum 23 and the direction perpendicular to the circumferential direction (i.e., the direction parallel to the axial direction of the cylindrical drum 23, which is indicated by letter X in FIG. 6(a)).

As illustrated in FIG. 1, the continuous diaper web 10 is introduced by unshown guide rollers at a predetermined tension onto the outer side of the support member 21 defining the periphery of the cylindrical drum 23 rotating in the direction indicated by arrow A, is carried a prescribed circumferential distance by the rotation of the drum 23 so as to be partly wrapped around the support member 21, and released from the support member 21 by unshown guide rollers, nip rollers, or the like. In that way, while the continuous diaper web 10 is wrapped around the support member 21 defining the periphery of the cylindrical drum 23 at a prescribed tension and being carried in contact with the pressing belt 24 pressing thereagainst, the portion of the continuous diaper web 10 sandwiched between the support member 21 and the pressing belt 24 and its vicinity are in a pressed (compressed) state in the thickness direction before being severed by laser beam irradiation. Thus, the continuous diaper web 10 is compressed more effectively particularly when it includes nonwoven fabric. Consequently, when the continuous diaper web 10 in such a compressed state is severed by a laser beam, the severed edges of the plurality of sheets constituting the severed region (the outer cover assembly 3) are fusion bonded to one another more securely thereby to assure further improved fusion bonding strength of the side seams 4.

The circumferential angular distance where the support member 21 (or the cylindrical drum 23) rotates between the introduction and the release of the continuous diaper web 10 may be, for example, 90° to 270°, preferably 120° to 270°. The circumferential angular length of the part of the continuous diaper web 10 that is pressed against the support member 21 by the pressing belt (hold down member) 24 (i.e., wrap angle) is preferably 90° to 270°, more preferably 120° to 270°. The above defined angular length would be 360° if the web 10 is pressed against the whole circumference of the support member 21 (the cylindrical drum 23).

In the embodiment shown in FIGS. 1, 6(a), and 6(b), the continuous diaper web 10 is continuously introduced with one side thereof (hereinafter referred to as a first side 10a) contacting the outer periphery of the support member 21 that defines the periphery of the cylindrical drum 23 and that has slit-like openings 27 (light transmissive windows) through which a laser beam 30 is allowed to pass. The introduced continuous diaper web 10 is pressed by the pressing belt (hold down member) 24 against the support member 21. The region of the thus pressed continuous diaper web 10 where a side seam 4 is to be formed (hereinafter also referred to as a target region) is irradiated with a laser beam 30 from the side of the support member 21 through the opening 27, thereby to simultaneously accomplish severing the continuous diaper web 10 and fusion bonding the severed edges of the plurality of sheets (the outer cover assembly 3) in the pressed state to form a facing pair of side seams 4 (side seam forming step).

Figure 7A:
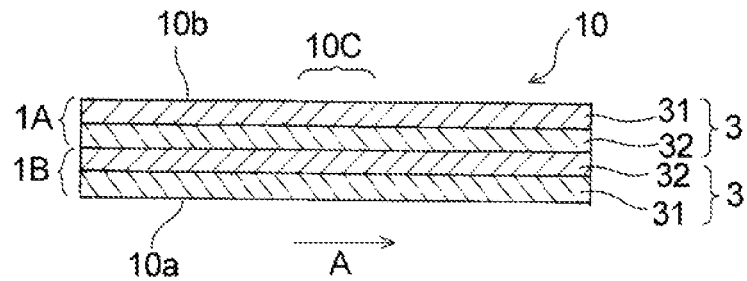
FIG. 7(a), FIG. 7(b), and FIG. 7(c) each illustrate a continuous diaper web (a continuous outer cover assembly web) being severed and fused to form side seams (sealed edge portions) simultaneously using the laser bonding device shown in FIG. 1.

FIG. 7 represents diagrams illustrating a continuous diaper web 10 (continuous superimposed sheets) being severed and fused simultaneously to form side seams (sealed edge portions) 4 using the laser bonding device 20. FIG. 7(a) schematically illustrates a predetermined target region 10C (the area where side seams 4 are to be formed by the laser beam 30) and its vicinity of the continuous diaper web 10. As illustrated in FIG. 6(a), the target region 10C is at the middle of the region of the continuous diaper web 10 in the longitudinal direction (machine direction A) where the absorbent assembly 2 is not disposed. The target region 10C includes: an 8-layered sub-region (in which 8 sheets are stacked) located in the edge portion of the waist opening 8 (see FIG. 2) and its vicinity and; a 4-layered sub-region (in which 4 sheets are stacked) in the rest. The 4-layered sub-region includes, as shown in FIG. 7(a), two sheets (the outer sheet 31 and the inner sheet 32) constituting the front portion 1A of the outer cover assembly 3 and two sheets (the outer sheet 31 and the inner sheet 32) constituting the rear portion 1B of the outer cover assembly 3, and formed by laminating these sheet. The 8-layered sub-region is in the above-described folded back portion along the edge portion 3a of the continuous outer cover assembly web 3. That is,  both side edge portions 3a of the outer cover assembly web 3 have been folded inward to cover the respective longitudinal end portions of the absorbent assembly 2 in the production of the continuous diaper web 10 (see FIGS. 4 and 5), so that there are two layers of the outer cover assembly 3 in each of the front portion 1A and the rear portion 1B. Since a total of 4 layers of the outer cover assembly 3 are stacked, there are eight sheets (31 and 32). Although every facing pair of sheets 31 and 32 in each of the 4-layered sub-region and the 8-layered sub-region may have elastic members, such as waist elastic members 5 and the below-waist elastic members 6, sandwiched therebetween, each drawing of FIG. 7 omits these elastic members for the sake of simplicity. While the description hereinafter given with respect to the side seams 4 will generally be confined to the 4-layered sub-region, it is equally applicable to the 8-layered sub-region.

Either one or both of the outer sheet 31 that defines the first side 10a (the surface in contact with the support member 21) of the target region 10C of the continuous diaper web 10 and the sheet other than the sheet defining the first side 10a (i.e., the inner sheet 32) are capable of absorbing a laser beam 30 to generate heat. In the embodiment illustrated, all the four sheets (i.e., sheets 31 and sheets 32) of the target region 10C are made of nonwoven fabric capable of absorbing a laser beam 30 to generate heat. The outer sheet 31 and the inner sheet 32 facing each other in the target region 10C and its vicinity may or may not have been bonded to each other by an adhesive, or the like before irradiation with a laser beam 30.

Figure 7B:
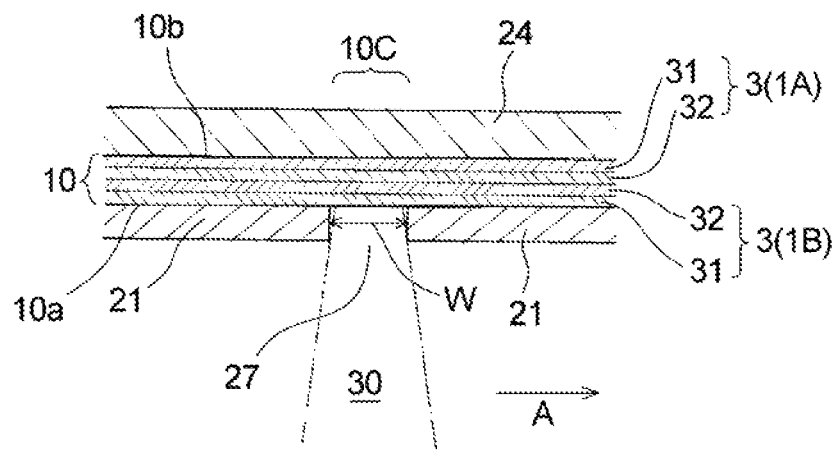

As illustrated in FIG. 7(b), the continuous diaper web 10 is introduced onto the support member 21 rotating in direction A such that the first side 10a contacts the support member 21 and that the target region 10c (the area where the side seam 4 is to be formed) is located at the slit-like opening 27 and, at the same time, the pressing belt (hold down member) 24 is applied under pressure onto the second side 10b. The continuous diaper web 10 is thus pressed (compressed) in its thickness direction while being conveyed in direction A. While being conveyed in a pressed state, the target region 10C is irradiated with a laser beam 30 from the side of the support member 21 through the opening 27. As stated earlier, the laser processing head is designed to move the irradiation point of the laser beam 30 freely in the circumferential direction of the cylindrical drum 23 following the circumferential movement of the opening 27. Therefore, the target region 10C located on the opening 27 is irradiated with the laser beam 30 continuously for a given time period while it is being conveyed.

Figure 7C:
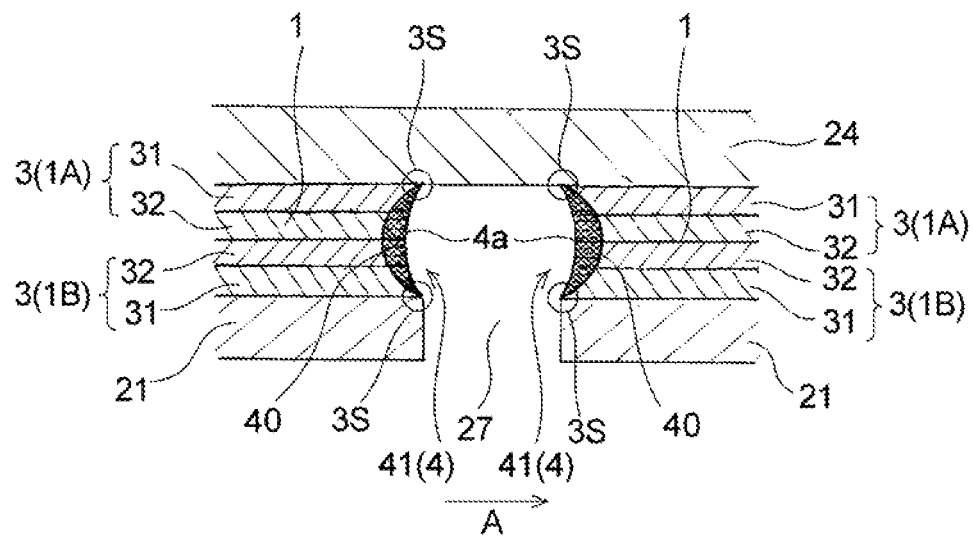

On being irradiated with the laser beam 30, the material (e.g., fiber) of the sheets 31 and 32 in the 4-layered target region 10C vaporizes and disappears due to the direct heat generated by the laser beam 30, and the material near the target region 10c is indirectly heated and melted by the laser beam 30. As a result, as illustrated in FIG. 7(c), the target region 10C having the 4-layered structure is severed by fusion to separate off a diaper precursor (superimposed sheets) from the continuous diaper web 10. Simultaneously with the fusion severing, the severed edges of the four sheets 31 and 32 of the separated diaper precursor are bonded to one another by fusion, and so are the severed edges of the four sheets 31 and 32 of the continuous diaper web 10. These severed edges have been in a pressed (compressed) state between the support member 21 and the pressing belt 24 before the severed edge formation (before the continuous diaper web 10 is severed by the irradiation with the laser beam 30). According to the method of the illustrated embodiment, severing of the continuous outer cover assembly web 3 and fusion bonding of a set of severed edges of the superimposed sheets of the outer cover assembly 3 and another set of severed edges of the superimposed sheets of the outer cover assembly 3 both in a pressed state are accomplished simultaneously just by a single pass of a laser beam. Compared with a method in which two target regions (one for one fusion-bonded seam) are fusion bonded by the respective passes of a laser beam, the method of the present embodiment achieves both fusion-bonding and severing in a single operation using almost half the laser output, allowing for efficient manufacture of the diaper 1.

The severed edges of the sheets 31 and 32 are in a molten state due to the heat generation during and immediately after irradiation with the laser beam 30. After the irradiation, the two sets of severed edges, one of the separated side-seamed diaper precursor and the other of the continuous diaper web 10, are each rapidly cooled to solidify by the outside air and through thermal conduction to the support member 21 and the pressing belt 24 while remaining in the pressed state between the support member 21 and the pressing belt 24, thereby to become a facing pair of fusion bonds 40 in which the material (e.g., fiber) of the severed edges is fused and united together. This formation of the fusion bonds 40 is formation of one of the pair of side seams 4 of one diaper 1. Where necessary, the severed edges of the sheets 31 and 32 may be positively cooled to accelerate the formation of fusion bonds 40 by use of a known cooling means, such as a suction means or an evacuation means.

After one target region 10C (the area to form side seams 4) is severed, the irradiation point of the laser beam 30 is moved backward relative to the web running direction (direction A) so that it may be located with the next opening 27 in the backward direction, where the laser beam is directed to the next target region 10C located on the next opening 27. Thus, the next target region 10C is severed and fusion bonded in the same manner as described above to form two side seams 4 (fusion bonds 40), the downstream one of which is paired with one of the previously formed side seams 4. Repetition of these operations achieves continuous production of the disposable pull-on diaper 1 having side-seamed outer cover assembly 3.

Figure 16:
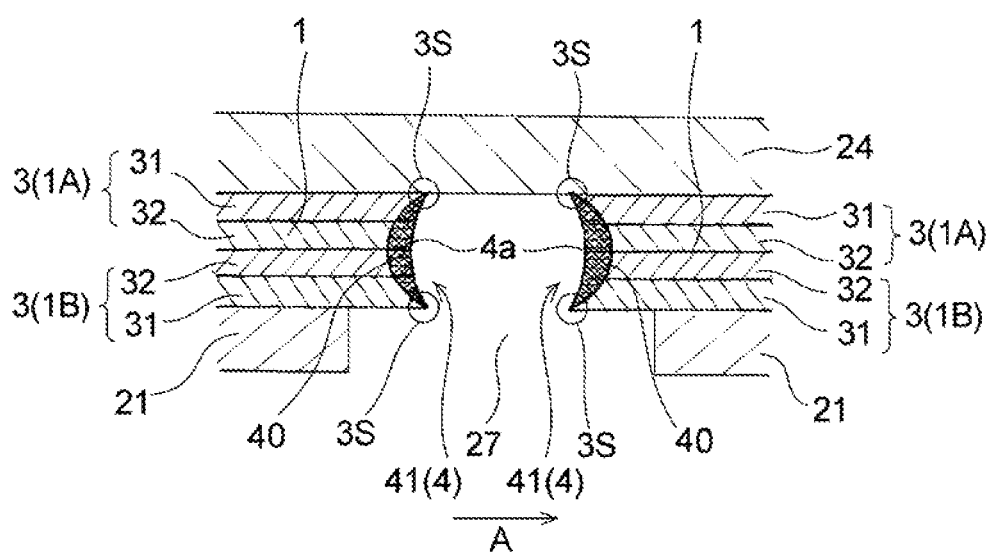
FIG. 16 is a view representing another embodiment of the method for making a disposable pull-on diaper using the laser bonding device shown in FIG. 1 (equivalent to FIG. 7(c)).

In the case when the diameter φ of the laser beam 30 (the diameter of an irradiated spot of the continuous diaper web 10 or the continuous superimposed sheets) is smaller than the width W of the slit-like opening 27 (the dimension of the opening 27 in the circumferential direction of the cylindrical drum 23, see FIG. 7(b)) (when φ/W<1), the facing pair of side seams 4 (fusion bonds 40) formed by the irradiation with the laser beam 30 can be located within the region of the continuous diaper web 10 that is located on the opening 27 (the region located between opposite longer sides of the opening 27 extending in the direction perpendicular to the machine direction A) as illustrated in FIG. 16. That is, the fusion bonds 40 can be formed even in a region of the continuous diaper web 10 that is not held between the support member 21 and the pressing belt (hold down member) 24 but near the edge of the opening 27, i.e., a region that is virtually under the influence of the pressing force exerted between the two members 21 and 24.

One of the characteristics of the thus produced diaper 1 resides in the structure of the side seams 4 in which the front body portion side edges 3F of the outer cover assembly 3 and the rear body portion side edges 3R of the outer cover assembly 3 are bonded to together at the respective continuous linear fusion bonds 40 extending in the longitudinal direction of the side seams to form sealed edge portions 41.

Figure 8A:
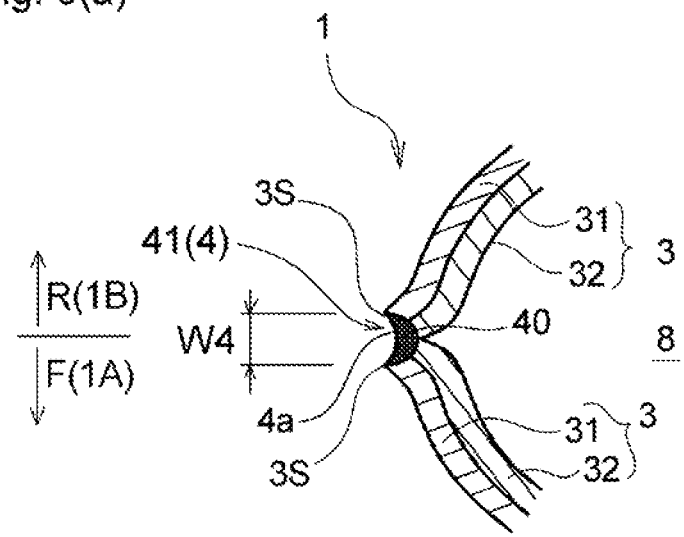
FIG. 8(a) and FIG. 8(b) are each a cross-sectional view of a side seam (sealed edge portion) and its vicinity of the diaper shown in FIG. 3 with the waist-opening wide open (equivalent to FIG. 3).
Figure 8B:
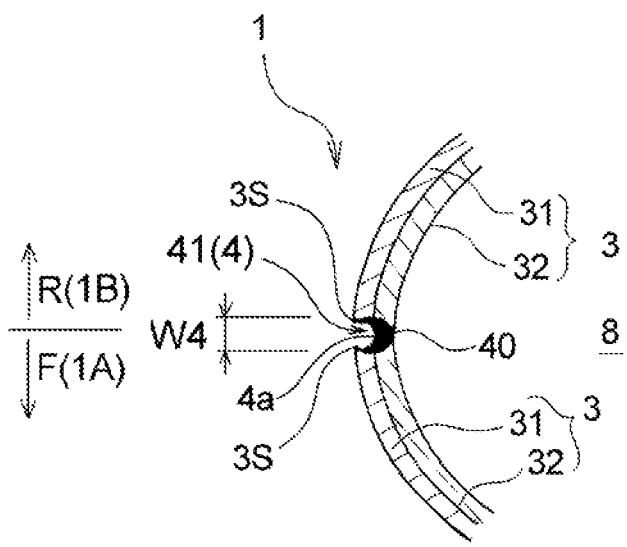

As illustrated in FIGS. 8(a) and 8(b), in a cross-sectional view taken in a direction perpendicular to the extending direction of the side seam 4, the exposed edge 4a of the fusion bond 40 of the sealed edge portion 41 is recessed toward an inner side of the pull-on garment, and the fusion bond 40 of the sealed edge portion 41 has a small width W4 when the exposed edge 4a is viewed from the side. The width W4 is preferably 5 mm or less, more preferably 3 mm or less, even more preferably 2 mm or less.

As illustrated in FIGS. 7(c) and 3, in a cross-sectional view taken in a direction perpendicular to the extending direction of the side seam 4 (i.e., the same direction as direction Y of the diaper 1), the exposed edge 4a of the fusion bond 40 of the sealed edge portion 41 resulting from the fusion severing is concave toward an inner side of the diaper 1 when the front portion 1A (the front body portion F) and the rear portion 1B (the rear body portion R) are in a mutually superimposed state, and the fusion bond 40, at which the four sheets 31 and 32 constituting the outer cover assembly 3 are bonded together, is formed along and inward of the exposed edge 4a. In the cross-sectional view, the fusion bond 40 is wider at the middle of the thickness of the outer cover assembly 3 (the vertical direction in FIG. 7(c) or 16) than at either of the opposite ends (the upper and lower ends). More specifically, in a cross-sectional view taken in lateral direction Y of the diaper 1 (the direction perpendicular to the laser severing direction), the fusion bond 40 has a gradually increasing width toward the middle in the diaper thickness direction, taking on a crescent or semicircular shape (the fusion bonds 40 illustrated in FIG. 7(c) has a crescent shape). The sealed edge portion 41 preferably has such a shape even when the diaper is worn.

In general, the side seam 4 tends to feel harder and less pleasant than the other part of the diaper 1 due to the presence of the fusion bond 40 formed by melting and solidification of the sheet-forming material and can be a cause of reducing the wearer comfort. When the fusion bond 40 is formed to take on a crescent or semicircular shape in a transverse cross-section of the diaper 1 as in the present embodiment, the proportion of the fusion bond 40 in an angular corner 3S of the side edge of the outer cover assembly 3 is smaller than that of a conventional side seam of which the fusion bond is rectangular in a transverse cross-section, such as the site indicated by numeral 9 in FIG. 1 of Patent Literature 1. Therefore, the softness and pleasant touch originally possessed by the outer cover assembly are less likely to be impaired at the corners 3S of the side seam 4 of the diaper 1, and the diaper 1 provides improved wearer comfort compared with the conventional diaper. On the other hand, there is a sufficient proportion of the fusion bond 40 in the middle portion of the side edge of the outer cover assembly 3 in the thickness direction of the outer cover assembly 3 (the portion between the corner 3S on the first side 10a and the corner 3S on the second side 10b of the outer cover assembly 3), which portion is largely influential on the fusion bond strength of the side seam 4. Therefore, the side seam 4 exhibits sufficient bond strength for practical use and is less likely to break during use of the diaper 1.

The diaper 1 is also characterized in that the side seams 4 (fusion bonds 40) are not easily recognizable from the outside while worn or in a relaxed, contracted state. In FIGS. 8(a) and 8(b) are shown a side seam 4 (fusion bond 40) of the diaper 1 with its waist opening 8 wide open while worn. With waist opening 8 wide open, the fusion bond 40 of the side seam 4 is usually exposed as illustrated in FIG. 8(a) but is hardly recognizable from the outside because, for one thing, the exposed edge 4a of the side seam 4 is concave toward an inner side of the outer cover assembly 3, and, for another, the fusion bond 40 is smaller than conventional side seams (fusion bonds). Depending on the material of the sheets 31 and 32, when the waist opening 8 is opened wide during use of the diaper 1, opposite corners 3S of the exposed edge of the outer cover assembly 3, one in the side of the front portion 1A and the other in the rear portion 1B, can come closer to each other to have a reduced distance therebetween as illustrated in FIG. 8(b) particularly because of the concavity of the exposed edge 4a of the side seam 4. Consequently, the fusion bond 40 located between the two corners 3S is made less touchable by the hand and less visually recognizable from the outside by the so close two corners 3S located outward of the fusion bond 40, which brings about improvement on not only the wearer comfort but also the outer appearance of the diaper 1.

The laser beam will next be described. The laser beam to be directed to the continuous diaper web 10 (continuous outer cover assembly web 3) should have an oscillation wavelength capable of being absorbed by any sheet constituting the outer cover assembly 3 (the outer sheet 31 and/or the inner sheet 32) and causing the sheet to heat. The sheet constituting the outer cover assembly as referred to herein is not limited to the sheet defining the first side 10a (the surface in contact with the support member 21) of the outer cover assembly, for example, the outer sheet 31 in the aforementioned embodiment, and may be any of the sheets constituting the outer cover assembly. Whether a laser beam directed to the outer cover assembly has an oscillation wavelength capable of being absorbed by any sheet of the outer cover assembly to cause the sheet to heat depends on the relationship between the sheet material and the wavelength of the laser beam. In the case where a sheet making up the outer cover assembly is nonwoven fabric or film made of a synthetic resin generally used in the manufacture of sanitary absorbent articles, such as disposable diapers and sanitary napkins, examples of preferred laser light sources include $CO_2$ lasers, YAG lasers, LD lasers (semiconductor lasers), $YVO_4$ lasers, and fiber lasers. In the case when a sheet making up the outer cover assembly contains, as a synthetic resin, polyethylene, polyethylene terephthalate, polypropylene, and so on, the oscillation wavelength capable of being absorbed by the sheet and causing the sheet to heat well is preferably, for instance, 8.0 to 15.0 μm. It is particularly preferred to use wavelengths of 9.0 to 11.0 μm emitted from $CO_2$ lasers available as high output lasers. The beam diameter, output, and so forth are selected as appropriate to the material and thickness of the sheets making up the outer cover assembly.

[II] Side Seam Visibility Improving Means

The above illustrated diaper 1 as a product obtained using the laser bonding device (i.e., the diaper 1 having a pair of side seams 4 that are formed by the step of severing and fusion bonding the outer cover assembly 3 at the same time) exhibits good softness and pleasant feel to the touch along its side seams 4 and thus provides improved wearer comfort. However, as stated earlier by way of FIGS. 2 and 8, the side seams 4 do not protrude outwardly from the neighboring part on the exterior or interior side at least when in use, and both the interior and the exterior surfaces of the diaper 1 do not substantially change around the side seams. Consequently, the side seams 4 are hard to recognize from the outside, i.e., have low visibility to the naked eye.

With such low visibility of the side seams 4, when, for example, a caregiver, e.g., the mother of an infant wearer, takes off the diaper from the wearer after use, there will be a likelihood that the caregiver has trouble finding the side seams 4 and removing the diaper 1. According to the invention, therefore, the diaper 1 is provided with a side seam visibility improving means in order to improve the visual recognizability of the side seams 4.

The pull-on garment of the invention and the method for making the garment of the invention will be described based on their preferred embodiments with reference to the accompanying drawings. The description of the embodiments hereinafter given will generally be confined to the difference from the fundamental technique discussed hereinabove. Other similar parts are indicated by similar numerals or references and will not be redundantly described. Unless the context is specifically otherwise, the description of the fundamental technique applies equally to the embodiments described infra.

In FIG. 9 is illustrated a disposable pull-on diaper 50A as a first embodiment of the pull-on garment of the invention.

Each of side seams 4A of the first embodiment diaper 50A has a sealed edge potion 41 in which the front body portion side edge 3F of the outer cover assembly 3 and the rear body portion side edge 3R of the outer cover assembly 3 are bonded to each other at a continuous linear fusion bond 40 extending in the longitudinal direction of the side seam 4A similarly to the pair of side seams 4 of the aforementioned diaper 1. The structure of the sealed edge portion 41 and the method for foiming the same are the same as described supra.

The first embodiment diaper 50A differs from the diaper 1 in that there is a non-sealed portion 42 in part of the side seam 4A, in which part of the front body portion side edge 3F and part of the rear body portion side edge 3R face to each other in a non-bonded relationship.

At least while the pull-on garment of the invention is worn, the front body portion side edge 3F and the rear body portion side edge 3R in each non-sealed portion 42 face each other in the wearer's body circumferential direction. The front body portion side edge 3F and the rear body portion side edge 3R in the non-sealed portion 42 may be in butting position but preferably create a gap therebetween at least while the diaper 50A is in use. In the non-sealed portion 41, the cut edge of the outer sheet 31 and the cut edge of the inner sheet 32 of each of the front body portion 3F and the rear body portion 3R are fusion bonded to each other.

The side seams 4A of the first embodiment diaper 50A are excellent in softness and feel to the touch because the sealed edge portions 41 of the side seams 4A are formed in the same manner as for the sealed edge portion 41 of the diaper 1. In addition, because the non-sealed portion 42 functions as a side seal visibility improving means, the side seams 4A have excellent visual recognizability.

To ensure visual recognizability of the side seams 4A, it is preferred that, while the garment is worn, the wearer's skin be seen from the outside through the gap formed between the unboded edges 3F, 3R in the non-sealed portion 42.

In order to secure the fusion bond strength required of the side seam 4A as well as to improve visual recognizability of the side seam 4A, the ratio of the length L2 of the non-sealed portion 42 to the total length L4 of the side seam 4A (the sum of the length of the sealed edge portions 41 and the non-sealed portion 42) is preferably 1% or more, more preferably 2% or more, and preferably 40% or less, more preferably 35% or less. Taking, for instance, a pull-on garment for infants of which the side seams 4A have a total length L4 of 100 mm, the length L2 of the non-sealed portion 42 is preferably 2 mm or more, more preferably 4 mm or more, and preferably 40 mm or less, more preferably 35 mm or less.

In the first embodiment diaper 50A, the front body portion F of the outer cover assembly 3 and the rear body portion R of the outer cover assembly 3 are each composed of two sheets 31 and 32 and elastic members 6 arranged therebetween. As illustrated in FIG. 9(b), the parts of the front body portion F and the rear body portion R of the outer cover assembly 3 that are located on either side of the non-sealed portion 42 contain at least one elastic member 6. Therefore, the gap between edges of the non-sealed portion 42 is broadened by the contraction of the elastic member 6 while the diaper is worn, thereby to further increase the visual recognizability of the side seam 4A.

Figure 10:
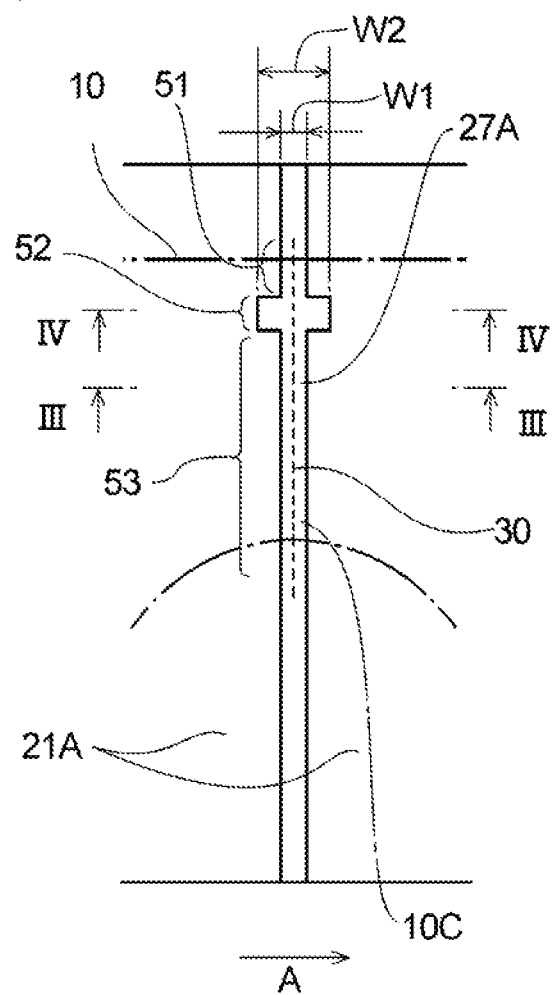
FIG. 10 is equivalent to a partial enlarged view of FIG. 6(a) in a first embodiment of the method according to the invention.

In a first embodiment of the method for making the pull-on garment of the invention, the first embodiment diaper 50A is produced in the same manner as described with respect to the fundamental technique, except that the support member 21 of the laser bonding device 20 is a support member 21A having, as a light transmissive window, an opening 27A. The opening 27A has a wide portion 52 and a narrow portions 51 and 53 different in width as illustrated in FIG. 10.

Figure 11:
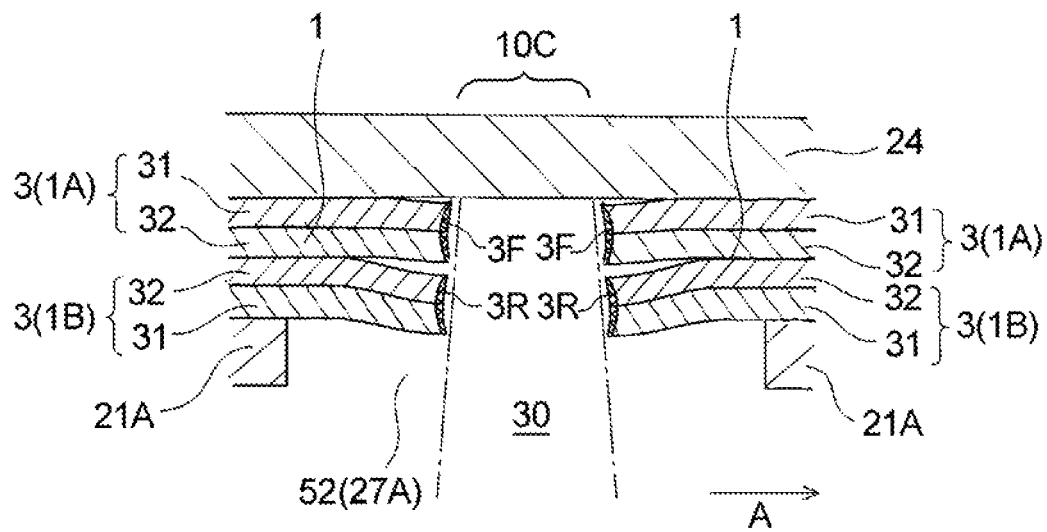
FIG. 11 illustrates a continuous diaper web (continuous outer cover assembly web) being severed, along a region where a non-sealed portion of a side seam is to be formed, using a laser bonding device in the first embodiment method of the invention (equivalent to FIG. 7(c)).

Specifically, the continuous diaper web 10 having the front and rear body portions superimposed on each other (the continuous outer cover assembly web 3) is introduced onto the cylindrical drum 23, the periphery of which is formed of the support member 21A, and pressed between the pressing belt 24 and the support member 21A. As illustrated in FIG. 1, a laser beam 30 is applied through the opening 27A to the target region 10C of the pressed continuous diaper web 10 (continuous outer cover assembly web 3). According to the first embodiment method, the subregions of the target region 10C that are to be irradiated with a laser beam through the narrow portions 51 and 53 are in a pressed state so that the plurality of layers of the outer cover assembly in these subregions are in tight contact with each other. Therefore, upon being irradiated with the laser beam 30, severing and fusion bonding of the severed edges of the superimposed body portions of the outer cover assembly 3 occur in these subregions. On the other hand, the subregion of the target region 10C that is to be irradiated with a laser beam through the wide portion 52 is in a less pressed state and therefore has the plurality of layers of the outer cover assembly superimposed in a less tight configuration. Upon being irradiated with the laser beam 30 through the wide portion 52, the subregion in such a less pressed state undergoes severing but is less susceptible to fusion bonding between the severed edges of the superimposed layers of the outer cover assembly 3 as illustrated in FIG. 11. FIG. 11 is a cross-sectional view of the subregion irradiated with a laser beam through the wide portion 52 (taken along line IV-IV in FIG. 10). The subregion irradiated with a laser beam through the narrow portion 53 (taken along line in FIG. 10) takes on the same cross-sectional profile as those shown in FIG. 7(c) and FIG. 16.

In the first embodiment method, the ratio of the width of the wide portion 52 to the width of the narrow portions 51 and 53 in designing the opening 27A (light transmissive window) and the conditions of laser beam irradiation through the wide portion 52 and the narrow portions 51 and 53 are decided appropriately so as to form the sealed edge portions 41 having the same structure as the sealed edge portion of the diaper 1 by irradiation through the narrow portions 51 and 53, and so as to form the non-sealed portion 42, where the front body portion side edges 3F and the rear body portion side edges 3R of the outer cover assembly face each other in a non-bonded relationship, by irradiation through the wide portion 52. As shown in FIG. 10, the laser beam 30 may simply scan in a straight line along the center of the slit-like opening 27A from one end to the other in the axial direction of the cylindrical drum with a constant beam diameter at a constant laser output.

In the embodiment shown in FIG. 11, an adhesive is present between the superimposed outer and inner sheets 31 and 32 in each of the front and rear body portions in and near the target region 10C before irradiation with the laser beam 30. When an adhesive is absent between the two sheets 31 and 32, the two sheets in each of the front and rear body portions are likely to be unbonded along the facing severed edges of the non-sealed portion 42.

According to the first embodiment method, the sealed edge portions 41 having softness and pleasant feel to the touch and the non-sealed portion 42 imparting improved visual recognizability to the side seam 4A are efficiently formed by irradiating the target region with a laser beam through a light transmissive window having the wide portion 52 and the narrow portions 51 and 53 different in width.

The ratio of the width W2 of the wide portion 52 to the width W1 of the narrow portions 51 and 53, W2/W1, is decided suitably so as to form the sealed edge portions 41 and the non-sealed portion 51 and 53, and, for example, is preferably 0.001 or more, more preferably 0.002 or more, preferably 0.8 or less, more preferably 0.6 or less, and specifically preferably 0.001 to 0.6, more preferably 0.002 to 0.6.

To form the non-sealed portion 42 more certainly, it is preferred to blow air to the target region of the continuous diaper web (superimposed layers of the outer cover assembly) during or after laser beam irradiation. For the same purpose, it is also preferred to apply vibration to the continuous diaper web (superimposed layers of the outer cover assembly) after the laser beam irradiation.

Figure 12:
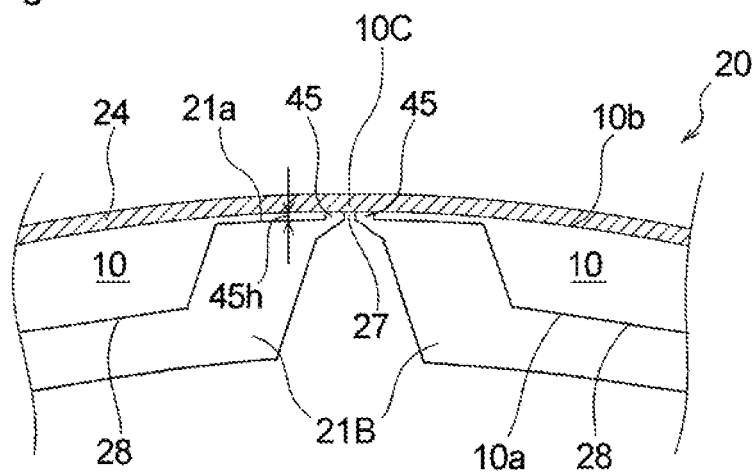
FIG. 12 is a schematic cross-sectional view of a light transmissive window and its vicinity of a laser bonding device used in a second embodiment of the method according to the invention.

FIG. 12 illustrates a second embodiment of the method for making the first embodiment diaper 50A. In the second embodiment method, a support member 21B having a high level portion 45a and a low level portion 45b different in height toward the side of the outer cover assembly is used as the support member 21 of the laser bonding device 20. The high level portion 45a and the low level portion 45b are located at the vicinity of the opening 27 (light transmissive window) and on an outer surface 21a of the support member on which the outer cover assembly web is to be contacted.

The light transmissive window allowing a laser beam to pass through provided in the laser bonding device 20 described with reference to the fundamental technique is a slit-like opening 27 going through the thickness of the support member 21. Therefore, a pressing force generated by the hold between the support member 21 and the pressing belt (hold down member) 24 is not directly exerted on the region of the continuous diaper web 10 (continuous outer cover assembly web 3) that is located on the opening 27, i.e., the target region 10C. Nonetheless, since the pressing force virtually has an influence on the target region, fusion bonds 40 are forming. In order to fond the fusion bonds more stably, it is effective to increase the pressing force by the hold between the two members 21 and 24.

Figure 13:
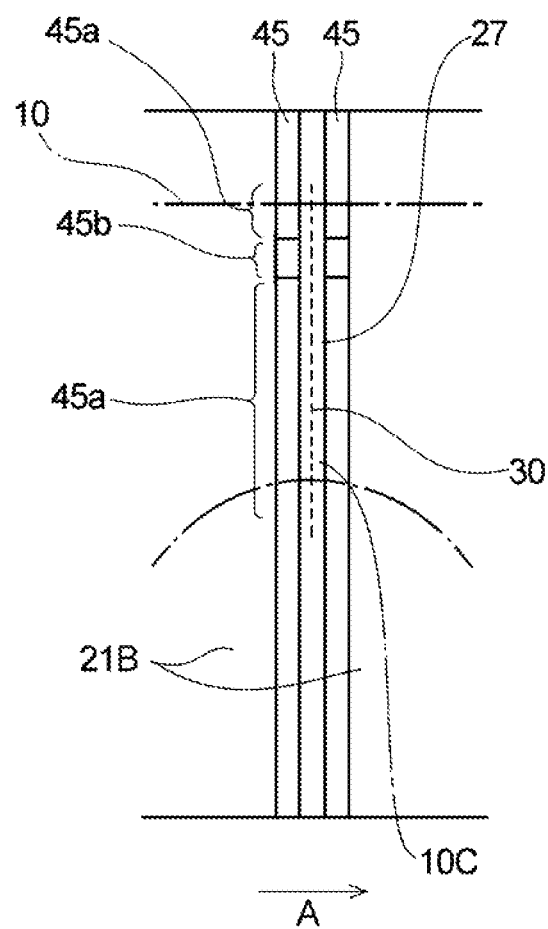
FIG. 13 is a view of a light transmissive window and its vicinity of the laser bonding device shown in FIG. 12, seen from the outside of a cylindrical drum on which a continuous diaper web (continuous outer cover assembly web) is to be placed.

As illustrated in FIGS. 12 and 13, the support member 21B used in the second embodiment method has, on the outer surface 21a thereof (on which the continuous diaper web 10 is introduced), a projection 45 projecting toward the web 10 (toward the pressing belt 24) on either side of, and close to, the slit-like opening 27 (within 35 mm from the edge of the opening 27). Specifically, the projection 45 is provided on the outer surface 21a of the support member 21B along each of the opposite edges, which extend in the longitudinal direction of the opening 27 (the transverse direction of the support member 21B), of every slit-like opening 27. Each projection 45 extends along the opening 27 in the longitudinal direction of the opening 27. Each projection 45 includes a low level portion 45b the height 45h of which (from the surface 21a adjoining the projection 45) is smaller than the other portion of the projection 45. The portion of the projection 45 other than the low level portion 45b is designated high level portions 45a. The low level portion 45a of each projection 45 has a smaller height 45h than the high level portion 45a of the projection 45. The top surface of each projection 45 may be flat or curved with a predetermined curvature radius. The curved top surface may be parallel to the surface 21a of the annular support member 21B.

The provision of the projection 45 having the high level portions 45a and the low level portion 45b by the side (along the edge) of the opening 27 on the outer surface 21a of the support member 21B allows for the following: effectively increasing the pressing force applied to near the subregion of the target region located near the high level portion 45a thereby to certainly sever the continuous diaper web 10 by fusion and securely form the sealed edge portion 41; and greatly reducing the pressing force applied to near the subregion of the target region located near the low level portion 45b as compared with that applied to near the high level portion 45a thereby to certainly form the non-sealed portion 42.

According to the second embodiment method, the diaper 50A the side seams 4A of which each include the sealed edge portions 41 having softness and pleasant feel to the touch and the non-sealed portion 42 that improves visual recognizability of the side seam 4A can be produced efficiently by directing a laser beam to regions strongly pressed by the high level portions 45a and a region weakly pressed by the low level portion 45b.

In order to assure the formation of the sealed edge portion 41 to secure a necessary fusion bond strength of the side seam 4A, the height 45h (see FIG. 12) of the high level portion 45a of the projection 45 is preferably 0.1 mm or more, more preferably 1 mm or more, preferably 10 mm or less, more preferably 8 mm or less, and specifically preferably 0.1 to 10 mm, more preferably 1 to 8 mm.

The difference in height between the low level portion 45b and the high level portion 45a is preferably 0.1 mm or more, more preferably 0.2 mm or more, specifically preferably 0.1 to 20 mm, more preferably 0.2 to 10 mm.

The low level portion 45b of the projection 45 does not need to be raised above the outer surface 21a of the support member 21B. That is, the low level portion 45b may be a portion which does not project from the outer surface 21a of the support member 21B at all.

Figure 14:
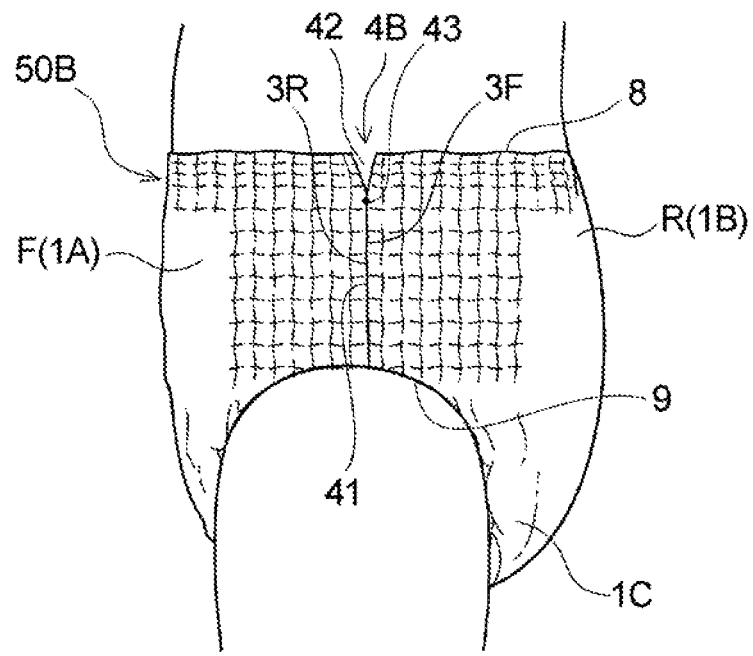
FIG. 14 is a side view of a second embodiment disposable pull-on diaper according to the invention.
Figure 15:
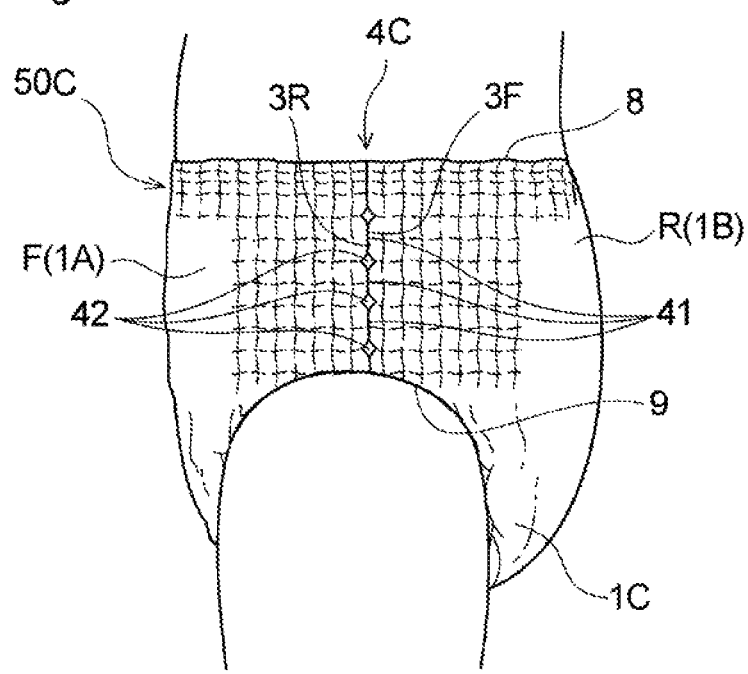
FIG. 15 is a side view of a third embodiment disposable pull-on diaper according to the invention.

FIGS. 14 and 15 illustrate other embodiments of the pull-on garment of the invention. FIG. 14 illustrates a second embodiment disposable pull-on diaper 50B. The diaper 50B has a non-sealed portion 42 at the end at the side of the waist opening 8 of each side seam 4B, one end of the non-sealed portion 42 being open to the waist opening 8. FIG. 15 illustrates a third embodiment disposable pull-on diaper 50C, in which each side seam 4C has a plurality of non-sealed portions 42 at intervals in its longitudinal direction, the non-sealed portions 42 each having the same structure as the non-sealed portion 42 of the first embodiment diaper.

According to the second and the third embodiment, since the side seams 4B and 4C of the diapers 50B and 50C, respectively, each have the same sealed edge portion 41 as that of the diaper 1, the side seams 4B and 4C exhibit softness and good feel to the touch. In addition, because the non-sealed portion 42 serves as a side seam visibility improving means, the side seams 4B and 4C are highly recognizable by the naked eye.

The second embodiment diaper 50B is produced by the same method as the first embodiment method of the invention, except for changing the position of the wide portion 52 to the location where to form the non-sealed portion 42 or the same method as the second embodiment method of the invention, except for changing the position of the low level portion 45b to the location where to form the non-sealed portion 42.

In the case when a non-sealed portion 42 open at the side of the waist opening 8 is formed as in the second embodiment diaper, an unintentional tear of the sealed edge potion 41 can initiate from the non-sealed portion 42 during wear. To avoid this, it is preferred that a tear-proof bond 43 for partly increasing the fusion bond strength be formed at a portion of sealed edge portion 41 near the non-sealed portion 42 in the longitudinal direction, as illustrated in FIG. 14.

The tear-proof bond 43 may be formed by, for example, increasing the laser beam intensity at the position where the tear-proof bond 43 is to be formed in applying the laser beam in a straight line along the longitudinal direction of the slit-like opening (light transmissive window) to form the sealed edge portion 41; additionally applying a laser beam only to the position where the tear-proof bond 43 is to be formed after the formation of the sealed edge portion 41; or previously applying a laser beam only to the position where the tear-proof bond 43 is to be formed before the formation of the sealed edge portion 41.

The third embodiment diaper 50C is produced by the same method as the first embodiment method of the invention, except for changing the number and the position of the wide portion 52 in agreement with the locations where to form the non-sealed portions 42 or the same method as the second embodiment method of the invention, except for changing the number and the position of the low level portion 45b in agreement with the locations where to form the non-sealed portions 42.

Figure 9A:
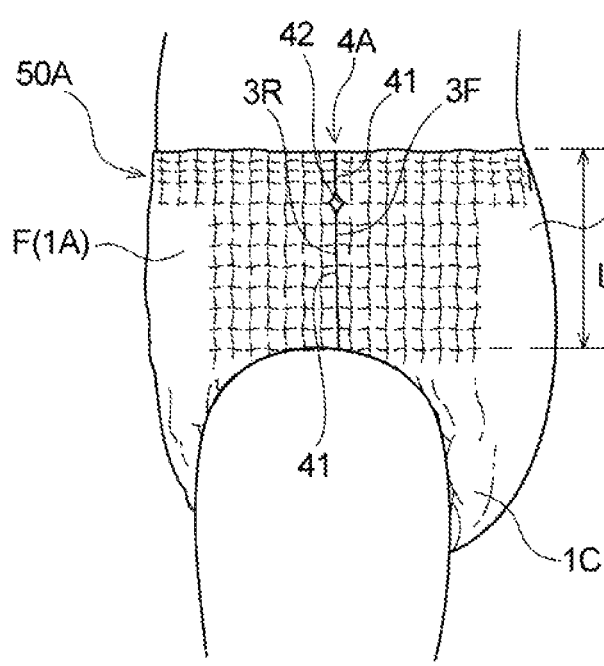
FIG. 9(a) is a side view of a disposable pull-on diaper as a first embodiment of the garment according to the invention.
Figure 9B:
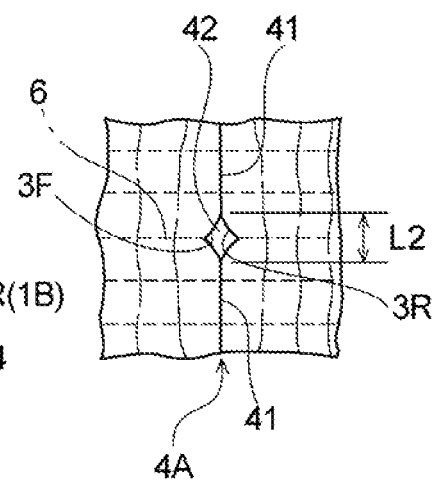
FIG. 9(b) is an enlarged view of a part of FIG. 9(a) showing a side seam and its vicinity.

In the case when a plurality of non-sealed portions 42 are formed in each side seam as in the third embodiment diaper 50C, in order to secure a fusion bond strength required of the side seam, the total of the lengths L2 of the individual non-sealed portions 42 is preferably 2% or more, more preferably 4% or more, and preferably 80% or less, more preferably 75% or less, relative to the total length L4 (see FIG. 9(a)) of the side seam. When a plurality of non-sealed portions 42 are formed in each side seam, the number of the non-sealed portions per seam is 2 or more, preferably 3 or more, preferably 80 or less, more preferably 75 or less, and specifically preferably 2 to 80, more preferably 3 to 75.

While the diaper 1 is worn or in a relaxed, contracted state, if the side seams 4 (fusion bonds 40) have low visual recognizability from the outside, a caregiver, e.g., the mother of an infant wearer, can have trouble finding the side seams 4 and removing the diaper 1 from the wearer after use. Means for eliminating such a disadvantage associated with the low visual recognizability include a method in which the color of the constituent member, of the diaper 1, which crosses the side seam 4, is changed between the front and the rear sides of the side seam 4. Specifically, the color of the waist elastic members 5 or the sheet (e.g., the outer sheet 31 or the inner sheet 32) making up the outer cover assembly 3 may be changed between the front portion 1A (front body portion) and the rear portion 1B (rear body portion).

According to this method, since the side seam 4 is located at the color change, the visual recognizability of the side seam is further improved, and the above discussed disadvantage is prevented from occurring more effectively.

It is only necessary in the invention that the severing of the continuous outer cover assembly web and the formation of bonds in the side seam forming step be carried out by fusing the outer cover assembly using a heat source. Means for fusing the outer cover assembly by use of a heat source is not limited to the above described laser light irradiation. For example, infrared light or halogen light may be used as a non-contact heat source. Other means are also usable, including heat-pressure application using a known heat roller unit or ultrasonication using a known ultrasonicator.

The severing of the continuous outer cover assembly web and the formation of bonds may be performed simultaneously, or the severing may follow the bond formation.

While the invention has been described based on its exemplary embodiments, the invention is not limited thereto, and various changes and modifications can be made therein as exemplified as follows.

For example, the superimposed outer cover assembly web (superimposed sheets) may be a stack of two, three, five or even more sheets as well as a stack of four sheets shown in FIG. 7(a). In order to wrap the continuous diaper web 10 around the cylindrical drum 23 (support member 21) without wrinkling or slack, the laser bonding device 20 may be equipped with a mechanism controlling the tension of the continuous diaper web 10.

While in the foregoing embodiments the outer cover assembly 3 is continuous from the front portion 1A, through the crotch portion 1C, to the rear portion 1B and is hourglass-shaped as shown in FIG. 4, the configuration of the outer cover assembly for use in the invention is not limited thereto. For example, the outer cover assembly may be separated into a front panel adapted to be worn about the front of a wearer and a rear panel adapted to be worn about the back of a wearer, and the absorbent assembly is fixed to the front and the rear panel to bridge them. In making this type of a disposable pull-on diaper, the aforementioned superimposing and pressing step is carried out by superimposing a continuous front part (front panel) web and a continuous rear part (rear panel) web, which are bridged by the absorbent assembly, on each other, and the target region (the area where side seams are to be formed) of the superimposed panels of the outer cover assembly (front and rear panels) is placed in a pressed state. This type of a pull-on garment, such as a disposable pull-on diaper, is also sectioned into a crotch portion, a front portion located forward of the crotch portion, and a rear portion located rearward of the crotch portion. The front panel is located in the front portion adapted to be applied to the front of a wearer, and the rear panel is located in the rear portion adapted to be applied to the back of a wearer. The rear panel and the front panel are connected to each other along their both lateral side edges (corresponding to the lateral sides of a pull-on garment) to form a pair of side seams.

While in the foregoing embodiments each side edge portion 3a of the continuous outer cover assembly web 3 (the continuous outer sheet 31 and the continuous inner sheet 32) extending in the machine direction is folded inward to cover each longitudinal end of the absorbent assembly 2 before the superimposing and pressing step as illustrated in FIG. 5, the manner of folding may be otherwise by using a continuous outer sheet 31 having a larger width than the continuous inner sheet 32 in the cross-machine direction. In this case, the sheets 31 and 32 are superimposed on each other such that the outer sheet 31 may extend from both side edges of the inner sheet 32, and each extending portion of the outer sheet 31 is folded inward to cover the corresponding longitudinal end of the absorbent assembly 2. Consequently, the target region 10C of the continuous diaper web 10 includes a 6-layered sub-region (in which 6 sheets are stacked) at the waist opening edge portion and its vicinity and a 4-layered sub-region (in which 4 sheets are stacked) in the rest. Each side edge portion 3a of the continuous outer cover assembly web 3 extending in the machine direction, i.e., each side edge portion of the continuous outer sheet 31 and the continuous inner sheet 32 does not always need to be folded inward.

The pull-on garment of the invention is not limited to disposable pull-on diapers and includes panty-type sanitary napkins and garments having the outer cover assembly defining the exterior surface but having no absorbent assembly, such as diaper covers.

With respect to particulars that have not been described for one embodiment, the corresponding details of other embodiments appropriately apply, and the feature described as being characteristic of one embodiment appropriately applies to other embodiments. Features of the aforementioned embodiments are interchangeable between the embodiments.

The following clauses are further disclosed with respect to the aforementioned embodiments of the invention (pull-on garments and methods for making the same).

[1] A pull-on garment comprising an outer cover assembly defining the exterior surface of the garment, the outer cover assembly having a front body portion and a rear body portion, the front body portion and the rear body portion of the outer cover assembly being connected to each other along their laterally opposite side edges to form a pair of side seams, a waist opening, and a pair of leg openings, the side seams each having: a sealed edge portion where the edge of the front body portion and the edge of the rear body portion of the outer cover assembly are bonded to each other at a continuous linear fusion bond extending in the longitudinal direction of the side seam; and, in part, a non-sealed portion where the edge of the front body portion and the edge of the rear body portion of the outer cover assembly face to each other in a non-bonded relationship.

[2] The pull-on garment according to clause [1], wherein the outer cover assembly comprises an outer sheet defining the exterior surface of the garment, an inner sheet disposed on the inner surface side of the outer sheet, and a plurality of thread-like or ribbon-like elastic members fixed between the outer sheet and the inner sheet with an adhesive.

[3] The pull-on garment according to clause [2], wherein the elastic members include waist elastic members forming waist gathers, below-waist elastic members forming below-waist gathers, and leg elastic members forming leg gathers each fixed in their stretch state at a predetermined stretch ratio between the outer sheet and the inner sheet.

[4] The pull-on garment according to clause [2] or [3], wherein the front body portion and the rear body portion of the outer cover assembly each have a waist elastic member forming waist gathers or a below-waist elastic member forming below-waist gathers, and the waist elastic member or the below-waist elastic member is fixed between the sheets constituting the outer cover assembly on either side of each side seam by an adhesive.

[5] The pull-on garment according to any one of clauses [1] to [4], wherein the outer cover assembly contains a resinous material and is formed mainly of the resinous material.

[6] The pull-on garment according to any one of clauses [1] to [5], wherein the outer cover assembly has nonwoven fabric, film, or a nonwoven fabric/film laminate.

[7] The pull-on garment according to any one of clauses [1] to [6], wherein, in a cross-sectional view taken in a direction perpendicular to the extending direction of the side seam, the sealed edge portion of each side seam has the fusion bond which is formed along its outer edge and at which the sheets constituting the outer cover assembly are bonded together, and the fusion bond has a larger width at the middle thereof than at both ends thereof in the thickness direction of the outer cover assembly.

[8] The pull-on garment according to any one of clauses [1] to [6], wherein, in a cross-sectional view taken in a direction perpendicular to the extending direction of the side seam, the sealed edge portion of each side seam has an exposed edge which is concave toward an inner side of the pull-on garment, and has the fusion bond at which the sheets constituting the outer cover assembly are bonded together along and inward of the exposed edge face, and the fusion bond has a larger width at the middle thereof than at both ends thereof in the thickness direction of the outer cover assembly.

[9] The pull-on garment according to any one of clauses [1] to [8], wherein the non-sealed portion is designed to create a gap between the edge of the front body portion and the edge of the rear body portion while the garment is worn such that the skin of a wearer is seen from the outside through the gap.

[10] The pull-on garment according to any one of clauses [1] to [9], wherein the front body portion and the rear body portion of the outer cover assembly are each composed of two sheets and elastic members arranged between the two sheets, the part of the front body portion and the part of the rear body portion of the outer cover assembly that are located on either side of the non-sealed portion each have at least one of the elastic members.

[11] The pull-on garment according to any one of clauses [2] to [10], wherein the non-sealed portion creates a wide gap between the edge of the front body portion and the edge of the rear body portion by the contraction of the elastic member when the pull-on garment is worn.

[12] The pull-on garment according to any one of clauses [1] to [11], wherein the non-sealed portion is one of a plurality of non-sealed portions spaced from each other in the longitudinal direction of each side seam.

[13] The pull-on garment according to any one of clauses [1] to [12], wherein the non-sealed portion is located at the end of each side seam at the side of the waist opening and opens to the waist opening,

[14] The pull-on garment according to any one of clauses [1] to [13], wherein each side seam has, near the non-sealed portion, a tear-proof bond for partly increasing the fusion bond strength of the sealed edge portion.

[15] The pull-on garment according to any one of clauses [1] to [14], wherein a member constituting the front side of each side seam and a member constituting the rear side of each side seam have different colors.

[16] The pull-on garment according to any one of clauses [1] to [15], wherein the pull-on garment has a crotch portion adapted to be worn about the crotch of a wearer while worn, a front portion located forward of the crotch portion, and a rear portion located backward of the crotch portion, and the color of a waist elastic member or a sheet making up the outer cover assembly is different between the front portion and the rear portion.

[17] The pull-on garment according to any one of clauses [1] to [16], wherein the pull-on garment has a crotch portion adapted to be worn about the crotch of a wearer while worn, a front portion located forward of the crotch portion, and a rear portion located backward of the crotch portion, and the outer cover assembly is continuous from the front portion, through the crotch portion, to the rear portion, and has an hourglass shape.

[18] The pull-on garment according to any one of clauses [1] to [17], wherein the pull-on garment has a crotch portion adapted to be worn about the crotch of a wearer while worn, a front portion located forward of the crotch portion, and a rear portion located backward of the crotch portion, the outer cover assembly is separated into a front panel adapted to be worn about the front of a wearer and a rear panel adapted to be worn about the back of a wearer, and the absorbent assembly is fixed to the front panel and the rear panel so as to bridge them.

[19] A method for making the pull-on garment according to any one of clauses [1] to [18], comprising:

a superimposing and pressing step in which the front body portion and the rear body portion of an outer cover assembly web are superimposed on each other, and a region of the superimposed front body portion and the rear body portion where a side seam is to be formed is placed in a pressed state and a side seam forming step in which the region where a side seam is to be formed is irradiated in the pressed state with a laser beam through a light transmissive window extending in a direction intersecting the machine direction of the outer cover assembly web thereby to sever the web and, at the same time, fusion-bond the edges of the superimposed front body portion and rear body portion resulting from the severing to form the side seam, the side seam forming step comprising irradiating the region where a side seam is to be formed with a laser beam through the light transmissive window having a wide portion and a narrow portion different in width, so that the sealed edge portion is formed by the laser beam which passes through the narrow portion, and the non-sealed portion is formed by the laser beam which passes through the wide portion.

[20] The method for making the pull-on garment according to clause [19], wherein the laser beam scans in a straight line along the center of the slit-like light transmissive window from one end to the other of the window in the axial direction of a cylindrical drum with a constant beam diameter at a constant laser output.

[21] The method for making the pull-on garment according to clause [19] or [20], wherein the side seam forming step is carried out using a support member having the light transmissive window having a wide portion and a narrow portion different in width.

[22] A method for making the pull-on garment according to any one of clauses [1] to [18], comprising:

a superimposing and pressing step in which the front body portion and the rear body portion of an outer cover assembly web are superimposed on each other, and a region of the superimposed front body portion and the rear body portion where a side seam is to be formed is placed in a pressed state and a side seam faulting step in which the region where a side seam is to be formed is irradiated in the pressed state with a laser beam through a light transmissive window extending in a direction intersecting the machine direction of the outer cover assembly web thereby to sever the web and, at the same time, fusion-bond the edges of the superimposed front body portion and rear body portion, the edges resulting from the severing to form the side seam, the side seam forming step being carried out using a support member having a high level portion and a low level portion different in height toward the side of the outer cover assembly web, the high level portion and the low level portion being located at the vicinity of the light transmissive window and on an outer surface of the support member on which the outer cover assembly web is to be contacted, the side seam forming step comprising applying the laser beam to; a region of the outer cover assembly web that is highly pressed by the high level portion to form the sealed edge portion; and to a region of the outer cover assembly web that is relatively weakly pressed by the low level portion to form the non-sealed portion.

[23] The method for making the pull-on garment according to clause [22], wherein the support member has, by the side of the light transmissive window and on its outer side on which the outer cover assembly web is contacted, a high level portion and a low level portion different in height toward the side of the outer cover assembly web.

[24] The method for making the pull-on garmet according to clause [22] or [23], wherein the height of the high level portion is preferably 0.1 mm or more, more preferably 1 mm or more, preferably 10 mm or less, more preferably 8 mm or less, and specifically preferably 0.1 to 10 mm, more preferably 1 to 8 mm.

[25] The method for making the pull-on garment according to any one of clause [22] to [24], wherein the difference in height between the low level portion and the high level portion is preferably 0.1 mm or more, more preferably 0.2 mm or more, specifically preferably 0.1 to 20 mm, more preferably 0.2 to 10 mm.

[26] The method for making the pull-on garment according to any one of clauses [19] to [25], wherein waist elastic members forming waist gathers, below-waist elastic members forming below-waist gathers, and leg elastic members forming leg gathers are arranged in their stretched state at predetermined stretch ratios between a continuous length of outer sheet and a continuous length of inner sheet constituting the outer cover assembly web which are continuously fed from the respective stock rolls.

[27] The method for making the pull-on garment according to any one of clauses [19] to [26], wherein the continuous outer sheet and the continuous inner sheet having the waist elastic members, the below-waist elastic members, and the leg elastic members fixed therebetween in their stretched state are introduced into the nip between a pair of nip rollers and pressed to make the continuous outer cover assembly web composed of the continuous sheets and the elastic members fixed between the continuous sheets in their stretched state.

[28] The method for making the pull-on garment according to any one of clauses [19] to [27], wherein a hot-melt adhesive is previously applied using an adhesive applicator to prescribed locations of one or both of the continuous outer sheet and the continuous inner sheet on the side facing to the other sheet before these continuous sheets are superimposed on each other.

[29] The method for making the pull-on garment according to any one of clauses [19] to [28], wherein, when the elastic members, such as the waist elastic members and the below-waist elastic members are provided in their stretched state to straddle regions to be severed by a laser beam, adhesive is previously applied to the regions and their vicinities.

[30] The method for making the pull-on garment according to any one of clauses [19] to [29], wherein a hot-melt adhesive is previously applied at intervals to the waist elastic members and the below-waist elastic members before they are arranged between the continuous outer sheet and the continuous inner sheet that constitute the outer cover assembly web.

[31] The method for making the pull-on garment according to any one of clauses [19] to [30], wherein, before irradiation with a laser beam, the outer sheet and the inner sheet which face each other and make the outer cover assembly are not bonded to each other in a region that is to be severed and a vicinity of the region that is to be severed.

[32] The method for making the pull-on garment according to any one of clauses [19] to [31], wherein the continuous outer cover assembly web has an absorbent assembly fixed thereto, and the outer cover assembly web is lengthwise folded to superimpose the front body portion and rear body portion of the web to make a continuous pull-on garment web having a plurality of seamless, pull-on garment precursors connected to each other in one direction.

[33] The method for making the pull-on garment according to any one of clauses [19] to [32], wherein, in the side seam forming step, a pair of the side seams is formed by irradiation with irradiation with the laser beam using a laser bonding device.

[34] The method for making the pull-on garment according to clause [33], wherein the side seam forming step is carried out using a laser bonding device to form the pair of side seams, the laser bonding device comprises: a rotatably driven, hollow cylindrical drum; an annular support member defining the outer periphery of the cylindrical drum; a laser processing head which is arranged inside the hollow cylindrical drum and from which head a laser beam is emitted toward the support member; a belt-type pressing unit having an endless pressing belt; and a tension adjusting mechanism for adjusting the tension of the pressing belt trained about the periphery of the annular support member, and the pressure applied to the continuous pull-on garment web by the support member and the pressing belt is adjusted by adjusting the tension.

[35] The method for making the pull-on garment according to any one of clauses [21] to [34], wherein the support member includes a light-transmissive window through which a laser beam is allowed to pass, and the support member includes, as the light-transmissive window, a slit-like opening which goes through the thickness of the support member.

[36] The method for making the pull-on garment according to any one of clauses [21] to [35], wherein the support member allows a laser beam to pass through the light transmissive window, but does not allow a laser beam to pass through a portion other than the light transmissive window.

[37] The method for making the pull-on garment according to any one of clauses [21] to [36], wherein the support member has a plurality of recesses on its peripheral surface (the surface with which the material to be processed is brought into contact) at a predetermined interval in the circumferential direction, the slit-like light transmissive window being formed in the region (i.e., a raised portion) between adjacent recesses.

[38] The method for making the pull-on garment according to any one of clauses [21] to [37], wherein the support member and the pressing belt have their temperatures maintained in a predetermined range by, for example, air cooling or water cooling.

[39] The method for making the pull-on garment according to any one of clauses [19] to [38], wherein air is blown to the region of the continuous pull-on garment web (superimposed layers of the outer cover assembly web) that is to be irradiated or has been irradiated with a laser beam either during or after the laser beam irradiation.

[40] The method for making the pull-on garment according to any one of clauses [19] to [39], wherein vibration is applied to the continuous pull-on garment web (superimposed layers of the outer cover assembly) after the laser beam irradiation.

[41] The method for making the pull-on garment according to any one of clauses [21] to [40], wherein the continuous pull-on garment web is introduced onto the rotating support member such that one side of the continuous pull-on garment web contacts the support member and that the region to be severed (the region where a side seam is to be formed) is located at the light transmissive window and, at the same time, the pressing belt (hold down member) is pressed against the other side of the continuous pull-on garment web so that the continuous pull-on garment web is pressed (compressed) in its thickness direction while being conveyed.

[42] The method for making the pull-on garment according to any one of clauses [21] to [41], wherein the region to be severed is irradiated with a laser beam from the side of the support member through the light transmissive window while it is being conveyed in a pressed state, and the laser processing head is designed to move the irradiation point of the laser beam freely in the circumferential direction of the cylindrical drum following the circumferential movement of the light transmissive window so that the region to be severed that is located on the light transmissive window is irradiated with the laser beam continuously for a given time period while the web is being conveyed.

[43] The method for making the pull-on garment according to any one of clauses [19] to [42], wherein the severing of the continuous outer cover assembly web and fusion bonding of two sets of severed edges, of the superimposed sheets of the outer cover assembly, both in a pressed state are accomplished simultaneously by a single irradiation with a laser beam.

[44] The method for making the pull-on garment according to any one of clauses [21] to [43], wherein the two sets of severed edges of the outer and inner sheets constituting the outer cover assembly web are in a molten state due to heat generation during and immediately after irradiation with the laser beam and, after the irradiation, the two sets of severed edges, one of the separated side-seamed diaper precursor and the other of the continuous pull-on garment web, are each rapidly cooled to solidify by the outside air and through thermal conduction to the support member and the pressing belt while remaining in the pressed state between the support member and the pressing belt, thereby to become a facing pair of fusion bonds in which the material of the severed edges is fused and united together.

[45] The method for making the pull-on garment according to any one of clauses [19] to [44], wherein a sheet making up the outer cover assembly is nonwoven fabric or film made of a synthetic resin, and the laser beam is from a laser light source, such as $CO_2$ lasers, YAG lasers, LD lasers (semiconductor lasers), $YVO_4$ lasers, and fiber lasers.

[46] The method for making the pull-on garment according to any one of clauses [19] to [45], wherein, when a sheet making up the outer cover assembly contains, as a synthetic resin, polyethylene, polyethylene terephthalate, polypropylene, or the like, a laser beam the oscillation wavelength of which is 8.0 to 15.0 μm is used.

[47] The method for making the pull-on garment according to any one of clauses [19] to [46], wherein the laser beam is emitted from a $CO_2$ laser having a wavelength of 9.0 to 11.0 μm.

[48] The method for making the pull-on garment according to any one of clauses [19] to [47], wherein the non-sealed portion comprises a non-sealed portion located at the end of each side seam at the side of the waist opening and opens to the waist opening and each side seam has, near the non-sealed portion located at the end of each side seam, a tear-proof bond for partly increasing the fusion bond strength of the sealed edge potion, the tear-proof bond being formed by increasing the laser beam intensity at the position where the tear-proof bond is to be formed in applying the laser beam in a straight line along the longitudinal direction of the slit-like light transmissive window to form the sealed edge portion; additionally applying a laser beam only to the position where the tear-proof bond is to be formed after the formation of the sealed edge portion; or previously applying a laser beam only to the position where the tear-proof bond is to be formed before the formation of the sealed edge portion.

INDUSTRIAL APPLICABILITY

The invention provides a side-seamed disposable pull-on garment of which the side seams are excellent in softness and feel to the touch and readily recognizable by the naked eye.

REFERENCE SIGNS LIST 1, 50A, 50B, 50C: disposable pull-on diaper (pull-on garment)
1A: front portion
1B: rear portion
F: front body portion
R: rear body portion
2: absorbent assembly
3: outer cover assembly
31: outer sheet
32: inner sheet
3F: front body portion side edge of outer cover assembly
3R: rear body portion side edge of outer cover assembly
4, 4A, 4B, 4C: side seam
40: fusion bond
4a: exposed edge
41: sealed edge portion
42: non-sealed portion
10: continuous diaper web (continuous outer cover assembly web)
20: laser bonding device
21, 21A, 21B: support member
26: belt-type pressing unit
27, 27A: opening (light transmissive window)
52: wide portion
53: narrow portion
30: laser beam
45: projection
45a: high level portion
45b: low level portion

The invention claimed is:

1. A pull-on garment comprising an outer cover assembly defining the exterior surface of the garment, the outer cover assembly having a front body portion and a rear body portion, the front body portion and the rear body portion of the outer cover assembly being connected to each other along their laterally opposite side edges to form a pair of side seams, a waist opening, and a pair of leg openings, the side seams each having: a sealed edge portion where the edge of the front body portion and the edge of the rear body portion of the outer cover assembly are bonded to each other at a continuous linear fusion bond extending in the longitudinal direction of the side seam; and, in part, a non-sealed portion where the edge of the front body portion and the edge of the rear body portion of the outer cover assembly face to each other in a non-bonded relationship, in a cross-sectional view taken in a direction perpendicular to the extending direction of the side seam, the sealed edge portion of each side seam having the fusion bond which is formed along its outer edge and at which the sheets constituting the outer cover assembly are bonded together, wherein the sealed edge portion of each side seam has an exposed edge which is concave toward an inner side of the pull-on garment and has the fusion bond at which the sheets constituting the outer cover assembly are bonded together along and inward of the exposed edge face, and the fusion bond having a larger width at the middle thereof than at both ends thereof in the thickness direction of the outer cover assembly.

2. The pull-on garment according to claim 1, wherein the outer cover assembly comprises an outer sheet defining the exterior surface of the garment, an inner sheet disposed on the inner surface side of the outer sheet, and a plurality of thread-like or ribbon-like elastic members fixed between the outer sheet and the inner sheet with an adhesive.

3. The pull-on garment according to claim 1, wherein the front body portion and the rear body portion of the outer cover assembly each have a waist elastic member forming waist gathers or a below-waist elastic member forming below-waist gathers, and the waist elastic member or the below-waist elastic member is fixed between the sheets constituting the outer cover assembly on either side of each side seam by an adhesive.

4. The pull-on garment according to claim 1, wherein the non-sealed portion is designed to create a gap between the edge of the front body portion and the edge of the rear body portion while the garment is worn such that the skin of a wearer is seen from the outside through the gap.

5. The pull-on garment according to claim 1, wherein the front body portion and the rear body portion of the outer cover assembly are each composed of two sheets and elastic members arranged between the two sheets, the part of the front body portion and the part of the rear body portion of the outer cover assembly that are located on either side of the non-sealed portion each have at least one of the elastic members.

6. The pull-on garment according to claim 2, wherein the non-sealed portion creates a wide gap between the edge of the front body portion and the edge of the rear body portion by the contraction of the elastic member when the pull-on garment is worn.

7. The pull-on garment according to claim 1, wherein the non-sealed portion is one of a plurality of non-sealed portions spaced from each other in the longitudinal direction of each side seam.

8. The pull-on garment according to claim 1, wherein the non-sealed portion is located at the end of each side seam at the side of the waist opening and opens to the waist opening.

9. The pull-on garment according to claim 1, wherein each side seam has, near the non-sealed portion, a tear-proof bond for partly increasing the fusion bond strength of the sealed edge portion.

10. The pull-on garment according to claim 1, wherein a member constituting the front side of each side seam and a member constituting the rear side of each side seam have different colors.

11. The pull-on garment according to claim 1, wherein the pull-on garment has a crotch portion adapted to be worn about the crotch of a wearer while worn, a front portion located forward of the crotch portion, and a rear portion located backward of the crotch portion, and the color of a waist elastic member or a sheet making up the outer cover assembly is different between the front portion and the rear portion.

12. The pull-on garment according to claim 1, wherein the pull-on garment has a crotch portion adapted to be worn about the crotch of a wearer while worn, a front portion located forward of the crotch portion, and a rear portion located backward of the crotch portion, and the outer cover assembly is continuous from the front portion, through the crotch portion, to the rear portion, and has an hourglass shape.

13. The pull-on garment according to claim 1, wherein the pull-on garment has a crotch portion adapted to be worn about the crotch of a wearer while worn, a front portion located forward of the crotch portion, and a rear portion located backward of the crotch portion, the outer cover assembly is separated into a front panel adapted to be worn about the front of a wearer and a rear panel adapted to be worn about the back of a wearer, and the absorbent assembly is fixed to the front panel and the rear panel so as to bridge them.

14. A method for making the pull-on garment according to claim 1, comprising:

a superimposing and pressing step in which the front body portion and the rear body portion of an outer cover assembly web are superimposed on each other, and a region of the superimposed front body portion and the rear body portion where a side seam is to be formed is placed in a pressed state and a side seam forming step in which the region where a side seam is to be formed is irradiated in the pressed state with a laser beam through a light transmissive window extending in a direction intersecting the machine direction of the outer cover assembly web thereby to sever the web and, at the same time, fusion-bond the edges of the superimposed front body portion and rear body portion resulting from the severing to form the side seam, the side seam forming step comprising irradiating the region where a side seam is to be formed with a laser beam through the light transmissive window having a wide portion and a narrow portion different in width, so that the sealed edge portion is formed by the laser beam which passes through the narrow portion, and the non-sealed portion is formed by the laser beam which passes through the wide portion.

15. A method for making the pull-on garment according to claim 1, comprising:

a superimposing and pressing step in which the front body portion and the rear body portion of an outer cover assembly web are superimposed on each other, and a region of the superimposed front body portion and the rear body portion where a side seam is to be formed is placed in a pressed state and a side seam forming step in which the region where a side seam is to be formed is irradiated in the pressed state with a laser beam through a light transmissive window extending in a direction intersecting the machine direction of the outer cover assembly web thereby to sever the web and, at the same time, fusion-bond the edges of the superimposed front body portion and rear body portion, the edges resulting from the severing to form the side seam, the side seam forming step being carried out using a support member having a high level portion and a low level portion different in height toward the side of the outer cover assembly web, the high level portion and the low level portion being located at the vicinity of the light transmissive window and on an outer surface of the support member on which the outer cover assembly web is to be contacted, the side seam forming step comprising applying the laser beam to; a region of the outer cover assembly web that is highly pressed by the high level portion to form the sealed edge portion; and to a region of the outer cover assembly web that is relatively weakly pressed by the low level portion to form the non-sealed portion.

16. The pull-on garment according to claim 1, wherein the edge of the front body portion in the sealed edge portion and the edge of the front body portion in the non-sealed portion are arranged in series along the extending direction in which the side seams extend.

17. The pull-on garment according to claim 1, wherein the edge of the back body portion in the sealed edge portion and the edge of the back body portion in the non-sealed portion are arranged in series along the extending direction in which the side seams extend.

* * * * *